(12) United States Patent
Akimoto

(10) Patent No.: US 11,432,713 B2
(45) Date of Patent: Sep. 6, 2022

(54) ENDOSCOPE SYSTEM, ENDOSCOPE IMAGE PROCESSING METHOD, AND COMPUTER READABLE RECORDING MEDIUM FOR GENERATING A THREE-DIMENSIONAL SHAPE IMAGE

(71) Applicant: OLYMPUS CORPORATION, Tokyo (JP)

(72) Inventor: Shunya Akimoto, Nishitokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 555 days.

(21) Appl. No.: 16/672,736

(22) Filed: Nov. 4, 2019

(65) Prior Publication Data
US 2020/0060528 A1 Feb. 27, 2020

Related U.S. Application Data

(63) Continuation of application No. PCT/JP2018/013153, filed on Mar. 29, 2018.

(30) Foreign Application Priority Data

Jun. 15, 2017 (JP) .............................. JP2017-117990

(51) Int. Cl.
*A61B 1/05* (2006.01)
*G02B 23/24* (2006.01)
(Continued)

(52) U.S. Cl.
CPC ............ *A61B 1/05* (2013.01); *A61B 1/00009* (2013.01); *G02B 23/24* (2013.01); *G06T 7/0012* (2013.01); *G06T 2207/10068* (2013.01)

(58) Field of Classification Search
None
See application file for complete search history.

(56) References Cited

U.S. PATENT DOCUMENTS 10,521,901 B2 * 12/2019 Ikemoto ................ G06T 7/0012
2009/0073257 A1 3/2009 Tanaka et al.
2018/0103246 A1 * 4/2018 Yamamoto ......... G02B 23/2415

FOREIGN PATENT DOCUMENTS

CN 101404924 A * 4/2009 .............. A61B 1/05
JP 2007-244517 A 9/2007
(Continued)

OTHER PUBLICATIONS

International Search Report dated Jun. 5, 2018 issued in PCT/JP2018/013153.

*Primary Examiner* — John P Leubecker
(74) *Attorney, Agent, or Firm* — Scully, Scott, Murphy & Presser, P.C.

(57) ABSTRACT

An endoscope system includes an endoscope configured to pick up an image of an inside of a subject to acquire an image, and a processor including hardware. The processor estimates a three-dimensional position of a target portion within the subject based on an image, sets for the three-dimensional position a reliability corresponding to a predetermined parameter related to the endoscope system determined when the image is acquired, and selects, when a plurality of three-dimensional positions for the target portion exist, a predetermined three-dimensional position among the plurality of three-dimensional positions depending on the reliability and generates a three-dimensional shape image.

15 Claims, 21 Drawing Sheets

(51) Int. Cl.
*G06T 7/00* (2017.01)
*A61B 1/00* (2006.01)

(56) References Cited

FOREIGN PATENT DOCUMENTS

| JP | 2014-144034 A | 8/2014 | | |
|----|---------------|--------|---|---|
| JP | 2014-161355 A | 9/2014 | | |
| JP | 2016-064281 A | 4/2016 | | |
| WO | WO-2016208664 A1 | * | 12/2016 | ............... A61B 1/00 |
| WO | WO 2017/081821 A1 | 5/2017 | | |

* cited by examiner

| IMAGE PICKUP POSITION | TARGET PORTION | THREE-DIMENSIONAL POSITION | TOTAL THREE-DIMENSIONAL POSITION |
|---|---|---|---|
| P3 |  |  |  |
| P2 |  |  | |
| P1 |  |  | |

ENDOSCOPE SYSTEM, ENDOSCOPE IMAGE PROCESSING METHOD, AND COMPUTER READABLE RECORDING MEDIUM FOR GENERATING A THREE-DIMENSIONAL SHAPE IMAGE

CROSS REFERENCE TO RELATED APPLICATION

This application is a continuation application of PCT/JP2018/013153 filed on Mar. 29, 2018 and claims benefit of Japanese Application No. 2017-117990 filed in Japan on Jun. 15, 2017, the entire contents of which are incorporated herein by this reference.

BACKGROUND OF THE INVENTION

1. Field of the Invention

The present invention relates to an endoscope system that estimates a three-dimensional position of a target portion within a subject based on an image acquired by an endoscope, an endoscope image processing method, and a computer readable recording medium.

2. Description of the Related Art

A technique for estimating a three-dimensional position of a target portion within a subject based on an image acquired by an endoscope has been conventionally proposed.

For example, Japanese Patent Application Laid-Open Publication No. 2014-161355 describes an endoscope apparatus including an image acquisition unit configured to acquire a picked-up image including an image of an object by image pickup of an image pickup unit, a distance information acquisition unit configured to acquire distance information based on a distance from the image pickup unit to the object at the time of image pickup, a brightness improvement unit configured to perform brightness adjustment processing for the picked-up image based on the distance information, and an image highlighting unit configured to perform highlighting processing for highlighting a structure of the object for the picked-up image after the brightness adjustment processing based on the distance information.

Japanese Patent Application Laid-Open Publication No. 2014-144034 describes an endoscope apparatus including an image acquisition unit configured to acquire a picked-up image including an image of an object, a distance information acquisition unit configured to acquire distance information based on a distance from an image pickup unit when the picked-up image is picked up to the object, an unevenness information acquisition unit configured to acquire unevenness information of the object as extracted unevenness information based on the distance information, a judgment unit configured to judge whether or not the extracted unevenness information is excluded or suppressed for each predetermined region of the picked-up image, and an unevenness information correction unit configured to exclude the extracted unevenness information in the predetermined region judged to be excluded or suppressed or suppressing an unevenness degree.

Further, Japanese Patent Application Laid-Open Publication No. 2016-64281 describes an endoscope apparatus including an image acquisition unit configured to acquire a picked-up image including an object image obtained by irradiating an object with illumination light from a light source unit, a region-of-interest setting unit configured to calculate a feature value based on the picked-up image and set a region of interest based on a region having a predetermined feature value, and a light-adjusting control unit configured to perform light-adjusting control of a light amount of illumination light based on the set region of interest.

SUMMARY OF THE INVENTION

An endoscope system according to an aspect of the present invention includes an endoscope configured to pick up an image of an inside of a subject to acquire an image, and a processor including hardware, in which the processor is configured to estimate a three-dimensional position of a target portion within the subject based on a predetermined image acquired by the endoscope, set for the estimated three-dimensional position a reliability corresponding to a predetermined parameter related to the endoscope system determined when the predetermined image is acquired, and select, when a plurality of three-dimensional positions for the target portion exist, a predetermined three-dimensional position among the plurality of three-dimensional positions depending on the set reliability and generate a three-dimensional shape image based on the selected predetermined three-dimensional position.

An endoscope image processing method according to an aspect of the present invention includes estimating a three-dimensional position of a target portion within a subject based on a predetermined image acquired by image pickup of an inside of the subject by an endoscope, setting for the estimated three-dimensional position a reliability corresponding to a predetermined parameter related to an endoscope system determined when the predetermined image is acquired, and selecting, when a plurality of three-dimensional positions for the target portion exist, a predetermined three-dimensional position among the plurality of three-dimensional positions depending on the set reliability and generating a three-dimensional shape image based on the selected predetermined three-dimensional position.

A computer readable recording medium according to an aspect of the present invention is a non-transitory computer readable recording medium storing an endoscope image processing program to be executed by a computer, the computer readable recording medium estimating, when a processor executes the endoscope image processing program, a three-dimensional position of a target portion within a subject based on a predetermined image acquired by image pickup of an inside of the subject by an endoscope, setting for the estimated three-dimensional position a reliability corresponding to a predetermined parameter related to an endoscope system determined when the predetermined image is acquired, and selecting, when a plurality of three-dimensional positions for the target portion exist, a predetermined three-dimensional position among the plurality of three-dimensional positions depending on the set reliability and generating a three-dimensional shape image based on the selected predetermined three-dimensional position.

DETAILED DESCRIPTION OF THE PREFERRED EMBODIMENTS

Embodiments of the present invention will be described below with reference to the drawings.

Embodiment 1

Figure 1:
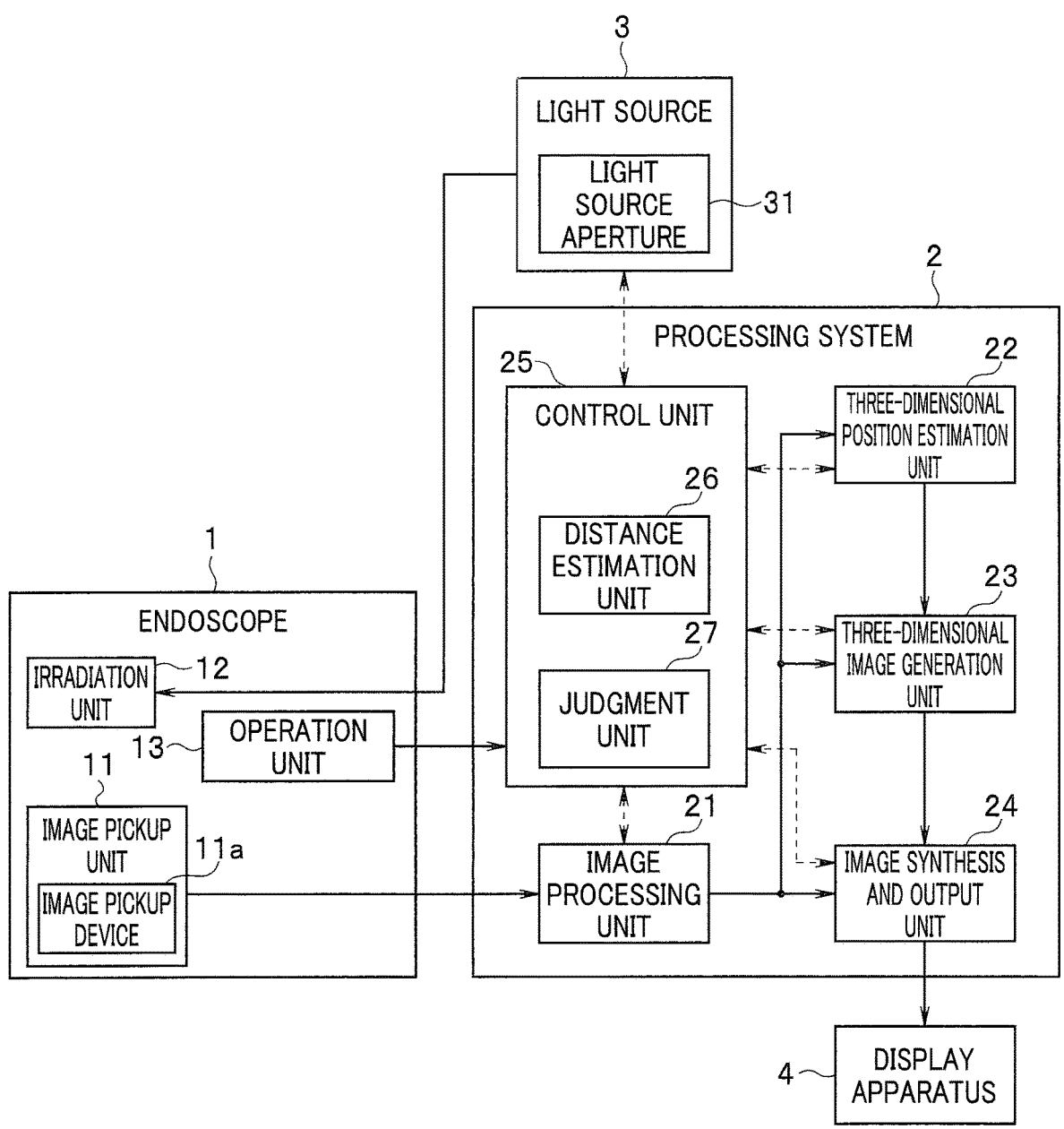
FIG. 1 is a block diagram illustrating a configuration of an endoscope system according to embodiment 1 of the present invention.

FIGS. 1 to 7 illustrate embodiment 1 of the present invention, where FIG. 1 is a block diagram illustrating a configuration of an endoscope system.

The endoscope system includes an endoscope 1, a processing system 2, a light source 3, and a display apparatus 4. Note that the processing system 2 and the light source 3 may be integral with each other, although they are separate from each other in the example illustrated in FIG. 1.

The endoscope 1 is an image acquisition apparatus configured to pick up an image of an inside of a subject having a three-dimensional shape to acquire an image, and includes an image pickup unit 11, an irradiation unit 12, and an operation unit 13. Among the units, the image pickup unit 11 and the irradiation unit 12 are arranged in a portion at a distal end 1a (see FIG. 6, etc.) of an insertion section in the endoscope 1, for example, and the operation unit 13 is consecutively provided on a hand side of the insertion section.

Note that although examples of the subject having a three-dimensional shape include a renal pelvis and a renal calyx of a kidney, the subject is not limited thereto, but is widely applicable for a subject capable of endoscope observation.

The irradiation unit 12 radiates illumination light transmitted from the light source 3 via a light guide, for example, toward an inside of the subject. The irradiation unit 12 may be configured as a light emitting source such as an LED and configured to emit illumination light with electric power supplied from the light source 3.

The image pickup unit 11 includes an image pickup device 11a, and forms an optical image of the inside of the subject irradiated with the illumination light using an objective optical system, picks up the formed optical image by performing photoelectric conversion using the image pickup device 11a, and generates and acquires a picked-up image.

The operation unit 13 performs various types of operations related to the endoscope 1 such as shooting of an image and a bending operation of a bending section when the insertion section is provided with the bending section.

The processing system 2 controls the endoscope 1 and the light source 3 while processing the picked-up image acquired from the endoscope 1 and generating image data for display. Further, the processing system 2 estimates a three-dimensional position D3P (see FIG. 6, etc.) within the subject based on the acquired image, generates a three-dimensional image within the subject as a guide image, for example, based on the estimated three-dimensional position D3P, and outputs the generated guide image to the display apparatus 4.

The processing system 2 includes an image processing unit 21, a three-dimensional position estimation unit 22, a three-dimensional image generation unit 23, an image synthesis and output unit 24, and a control unit 25. Note that the processing system 2 is configured to cause a processor including hardware such as a CPU to perform software (an endoscope image processing program recorded in a computer readable recording medium) to performs a function of each of the units within the processing system 2. The present invention is not limited to the configuration, but the processing system 2 may be configured by a processor including an electronic circuit (hardware) corresponding to each of the units within the processing system 2 or may be each of circuit units in a processor including an integrated circuit (hardware) such as an FPGA (field programmable gate array).

The image processing unit 21 subjects the picked-up image outputted from the image pickup unit 11 to various types of image processing such as concurrent processing (or demosaicking processing), white balance processing, color matrix processing, and gamma conversion processing, to generate an endoscope image.

The three-dimensional position estimation unit 22 estimates a three-dimensional position D3P of a target portion within the subject based on the image (the picked-up image acquired by the image pickup device 11a or the endoscope image processed by the image processing unit 21).

More specifically, the three-dimensional position estimation unit 22 estimates the three-dimensional position D3P of the target portion based on a distance from the distal end 1a of the endoscope 1 to the target portion in the subject, which has been estimated by a distance estimation unit 26, described below, and a position of the target portion in the image (a position of a pixel, in which the target portion appears, in the image).

A configuration of the objective optical system in the endoscope 1 has been known, and information such as an angle of view is previously found. At this time, an orientation of the target portion viewed from the distal end 1a of the endoscope 1 can be known depending on the position of the pixel, in which the target portion appears, in the image acquired by the endoscope 1. Therefore, the distance and the orientation of the target portion viewed from the distal end 1a of the endoscope 1, i.e., a three-dimensional position of the target portion relative to the endoscope 1 (a three-dimensional position in a relative coordinate system) can be known.

In the present embodiment, it is assumed that the endoscope 1 is arranged in a fixed positional relationship with the subject (a laparoscope, etc. as an example), that is, a position and an orientation of the endoscope 1 itself in an absolute coordinate system within a treatment chamber or the like is known.

Thus, the three-dimensional position D3P of the target portion in the absolute coordinate system is estimated by the three-dimensional position estimation unit 22.

The three-dimensional image generation unit 23 generates a three-dimensional shape image corresponding to a reliability based on the three-dimensional position D3P estimated by the three-dimensional position estimation unit 22.

More specifically, the three-dimensional image generation unit 23 calculates a polygon using a known method such as a ball-pivoting algorithm based on a plurality of three-dimensional positions D3P related to the subject estimated by the three-dimensional position estimation unit 22, and generates a three-dimensional shape image composed of a plurality of polygons (the three-dimensional shape image may represent only a shape by a configuration of the polygons or is obtained by attaching an endoscope image to each of the polygons).

The image synthesis and output unit 24 synthesizes the endoscope image generated by the image processing unit 21 and the three-dimensional shape image generated by the three-dimensional image generation unit 23 into one image and outputs the one image to the display apparatus 4. As a result, a user can perform treatment, for example, by inserting or removing the endoscope 1 while using the three-dimensional shape image as a guide via the display apparatus 4 and observing the inside of the subject by the endoscope image.

The control unit 25 is connected to the image processing unit 21, the three-dimensional position estimation unit 22, the three-dimensional image generation unit 23, and the image synthesis and output unit 24, described above, and controls the entire processing system 2 while also controlling the endoscope 1 and controlling ON/OFF of the light source 3, a light amount, and the like.

The control unit 25 includes the distance estimation unit 26 and a judgment unit 27.

The distance estimation unit 26 estimates a distance between the endoscope 1 and the subject based on an image. Examples of a method of estimating a distance from the distal end 1a of the endoscope 1 to the target portion in the subject based on the image by the distance estimation unit 26 include the following method.

Assuming that respective light reflectances of sites of the subject are the same, the farther the distance from the distal end 1a of the endoscope 1 is, the darker return light radiated from the irradiation unit 12 and reflected by the subject to return becomes. Conversely, the nearer the distance is, the brighter the return light becomes. A distance to the target portion in the subject can be estimated depending on a luminance of the image (a luminance of the target portion appearing in the image).

Note that although a method of estimating the distance between the endoscope 1 and the subject based on the luminance of the image has been described, the present invention is not limited to this. If the endoscope 1 is configured to include a plurality of image pickup units having a parallax, for example, the distance between the endoscope 1 and the subject may be calculated based on a phase difference among a plurality of images respectively obtained by the plurality of image pickup units. The endoscope system may be configured to include a distance image sensor based on a pattern irradiation system, a TOF (time of flight) system, or the like to calculate the distance between the endoscope 1 and the subject.

The judgment unit 27 judges a reliability for the three-dimensional position D3P estimated by the three-dimensional position estimation unit 22 based on a predetermined parameter related to the endoscope system. The predetermined parameter includes any one of a luminance of a target portion appearing in an image, a light source aperture value of a light source aperture 31 configured to control a light amount of illumination light to be radiated onto a subject, a gain of the image pickup device 11a configured to acquire an image, a position of a target portion appearing in an image relative to an optical center of the image, a hue of a target portion appearing in an image, a movement speed of the distal end 1a of the endoscope 1, and a reliability for a measurement value by a measurement section, described below, as described in the present embodiment and embodiments described below.

The light source 3 generates illumination light to be radiated onto the subject, and includes the light source aperture 31 configured to control a light amount of illumination light by restricting a light passage range.

The display apparatus 4 displays an image including the endoscope image and the three-dimensional shape image, which have been outputted from the image synthesis and output unit 24, to be observable.

Figure 2:
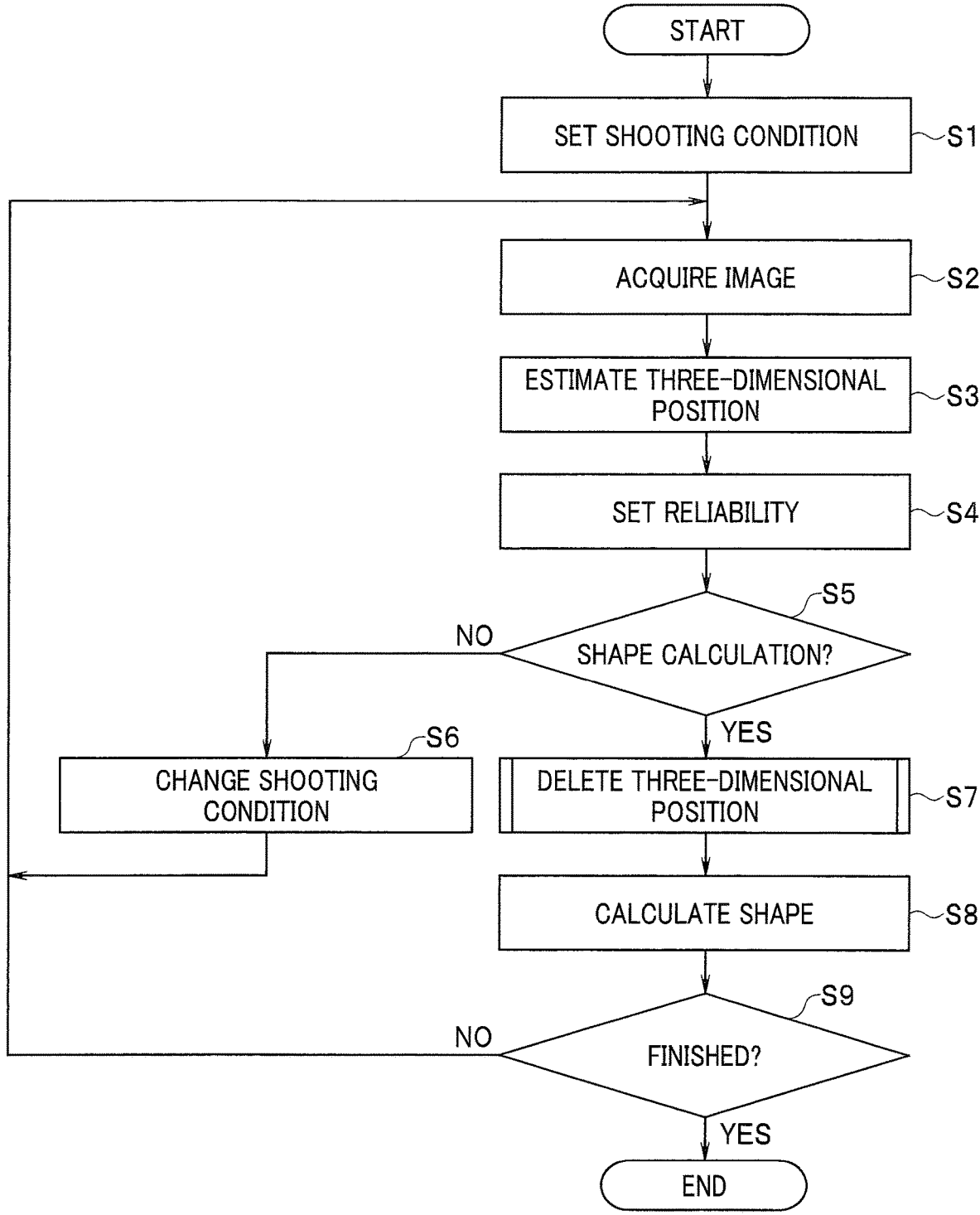
FIG. 2 is a flowchart illustrating a function of the endoscope system according to the above-described embodiment 1.

Then, FIG. 2 is a flowchart illustrating a function of the endoscope system.

If the processing is started when the endoscope 1 is installed at a predetermined position and in a predetermined orientation within a subject to determine a position and an orientation, the control unit 25 sets shooting conditions such as a light source aperture value of the light source aperture 31 in the light source 3 and a gain for a picked-up image to be outputted from the image pickup unit 11 such that a brightness of the image becomes a brightness having an initial value previously determined (step S1).

The image pickup device 11a performs exposure under the set shooting conditions, and outputs a generated picked-up image from the image pickup unit 11, to acquire an image (step S2). In the processing system 2, the image processing unit 21 processes the acquired picked-up image, to generate an endoscope image.

The distance estimation unit 26 estimates a distance from the distal end 1a of the endoscope 1 to a target portion within the subject appearing in a pixel at a determined position on the image using a luminance of the pixel, for example. The determined position generally includes a plurality of positions set on the image. Therefore, a distance to the target portion to be estimated from the one image also includes a plurality of distances.

The three-dimensional position estimation unit 22 estimates the three-dimensional position D3P of the target portion based on the distance to the target portion estimated by the distance estimation unit 26, a position within the image of the pixel in which the target portion appears, and a predetermined position and a predetermined orientation of the endoscope 1 (step S3).

The judgment unit 27 judges and sets the reliability for the three-dimensional position D3P estimated by the three-dimensional position estimation unit 22 (step S4).

Figure 3:
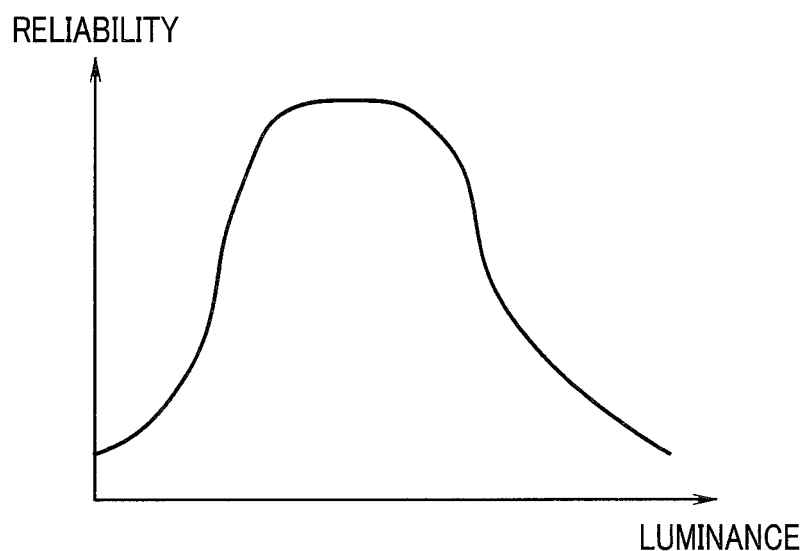
FIG. 3 is a diagram illustrating an example of a reliability set depending on a luminance in the endoscope system according to the above-described embodiment 1.
Figure 4:
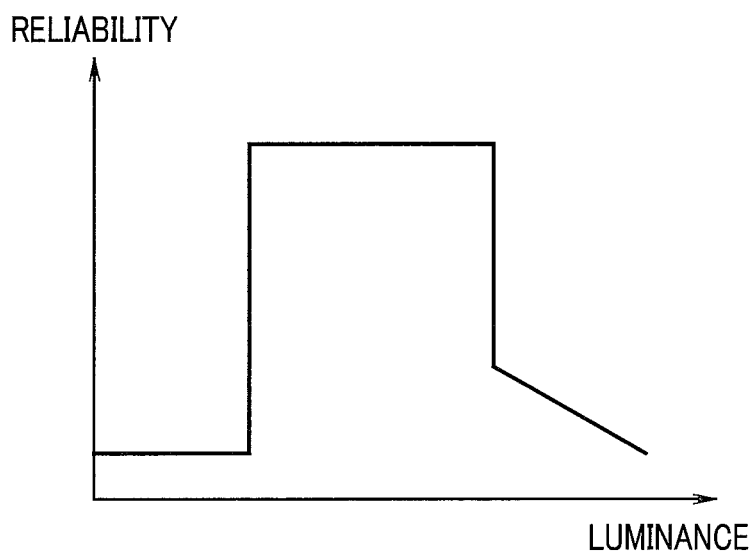
FIG. 4 is a diagram illustrating an example of a reliability simply set depending on a luminance in the endoscope system according to the above-described embodiment 1.

FIG. 3 is a diagram illustrating an example of a reliability set depending on a luminance, and FIG. 4 is a diagram illustrating an example of a reliability simply set depending on a luminance.

In the present embodiment, the reliability for the three-dimensional position D3P is judged and set, as illustrated in FIG. 3 or 4, depending on a luminance of a pixel used to estimate a distance. In other words, in the present embodiment, a luminance of a target portion appearing in an image is used as a predetermined parameter related to the endoscope system.

First, FIG. 3 illustrates an example in which the reliability is consecutively changed depending on the luminance. On the other hand, FIG. 4 illustrates an example including a portion where the reliability is inconsecutively changed depending on the luminance, where a curve illustrated in FIG. 3 is approximated with a polygonal line to simplify processing.

In both the examples illustrated in FIGS. 3 and 4, a low reliability is provided when the luminance of the pixel enters a low luminance area, a high reliability is provided when the luminance of the pixel enters a middle luminance area, and a reliability that monotonously decreases as the luminance of the pixel increases is provided when the luminance enters a high luminance area.

Note that since a reliability curve or the like illustrated in FIGS. 3 and 4 is one example, an appropriate reliability curve or the like may be constructed depending on a subject, a shooting environment, or the like.

If the reliabilities are respectively set for all the three-dimensional positions D3P estimated by the three-dimensional position estimation unit 22, the control unit 25 judges whether or not the processing proceeds to shape calculation processing (step S5).

If it is judged that the processing does not proceed to the shape calculation processing yet, the control unit 25 changes a shooting condition, i.e., values such as a light source aperture value of the light source aperture 31 and a gain for a picked-up image (step S6). Note that at this time, the position and the orientation of the endoscope 1 do not change because the predetermined position and predetermined orientation, described above, are maintained.

Under the shooting condition changed in step S6, the above-described process in step S2 is performed to acquire an image. When the processes in steps S2 to S6 are repeatedly performed a plurality of times, a plurality of images, which differ in shooting condition, are acquired, and a plurality of three-dimensional positions D3P are estimated for the same target portion within the subject based on the acquired plurality of images.

When a required number of images, which differ in shooting condition, have been gathered, it is judged in step S5 that the processing proceeds to the shape calculation processing, and the three-dimensional image generation unit 23 performs three-dimensional position deletion processing for deleting the plurality of three-dimensional positions D3P estimated for the same target portion depending on the respective reliabilities, as described below with reference to FIG. 5 (step S7).

The three-dimensional image generation unit 23 calculates a polygon using a ball-pivoting algorithm, for example, as described above, to generate a three-dimensional shape image composed of a plurality of polygons based on the three-dimensional positions D3P remaining after the three-dimensional position D3P for which the reliability is low has been deleted (step S8).

In other words, the three-dimensional image generation unit 23 deletes, when the plurality of three-dimensional positions D3P for the target portion exist, the three-dimensional positions D3P other than the three-dimensional position D3P for which the reliability is highest, and generates a three-dimensional shape image based on the three-dimensional positions D3P remaining after the deletion.

Then, it is judged whether or not the processing is finished (step S9). If it is judged that the processing is not finished, the processing returns to step S2. In step S2, subsequent image acquisition is performed. On the other hand, if it is judged that the processing is finished, the processing ends.

Figure 5:
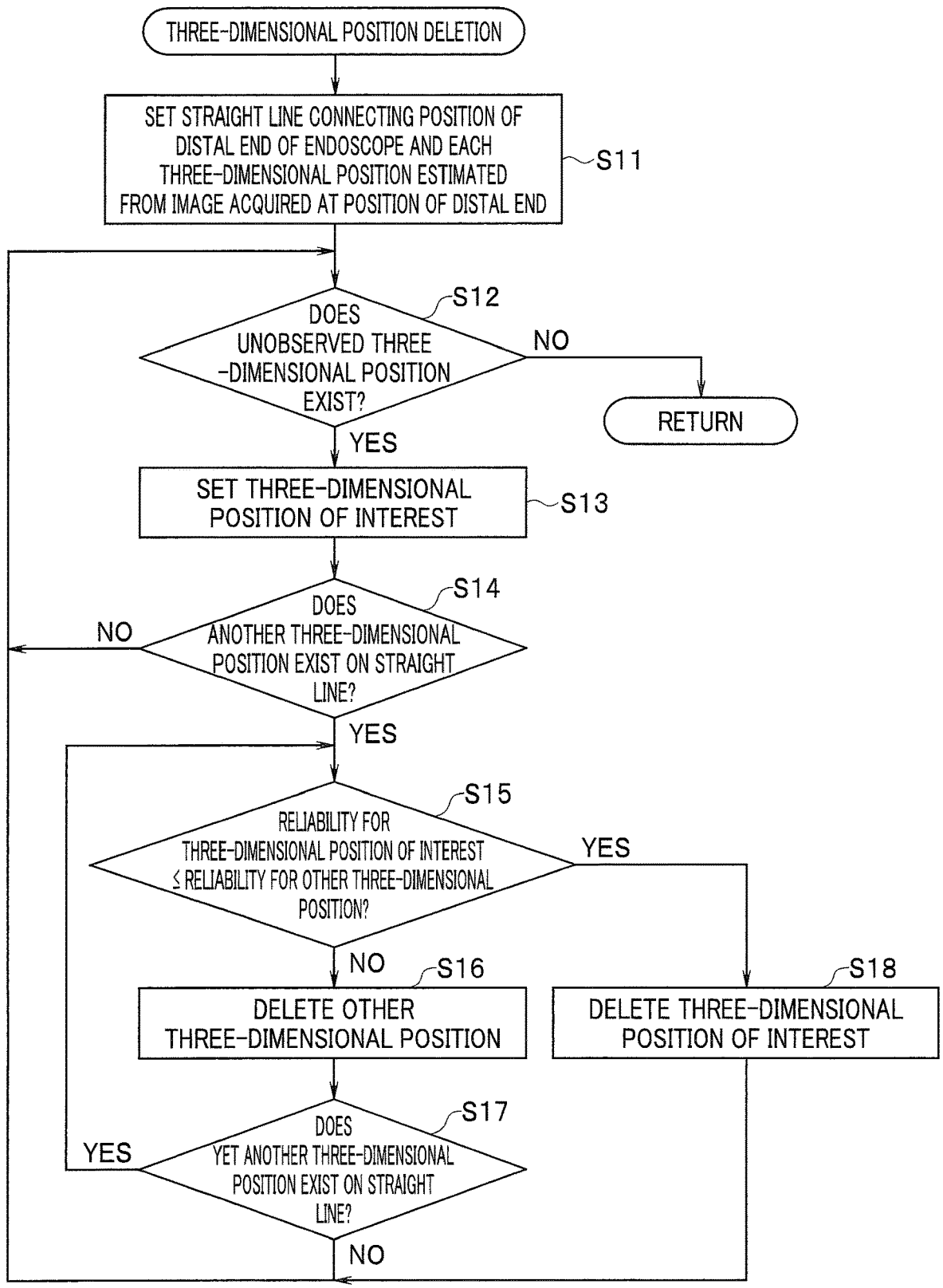
FIG. 5 is a flowchart illustrating three-dimensional position deletion processing in the endoscope system according to the above-described embodiment 1.

Then, FIG. 5 is a flowchart illustrating three-dimensional position deletion processing in the endoscope system.

If the processing is started, a straight line connecting a position of the distal end 1a of the endoscope 1 (see FIG. 6) and each of a plurality of three-dimensional positions D3P estimated from an image acquired at the position of the distal end 1a is set (step S11).

Note that the straight line is not limited to a straight line having an infinite length, but may be a line segment having a finite length (a line segment respectively having the position of the distal end 1a of the endoscope 1 and the three-dimensional position D3P as both ends), or may be a vector directed from either one of the position of the distal end 1a of the endoscope 1 and the three-dimensional position D3P to the other.

Figure 6:
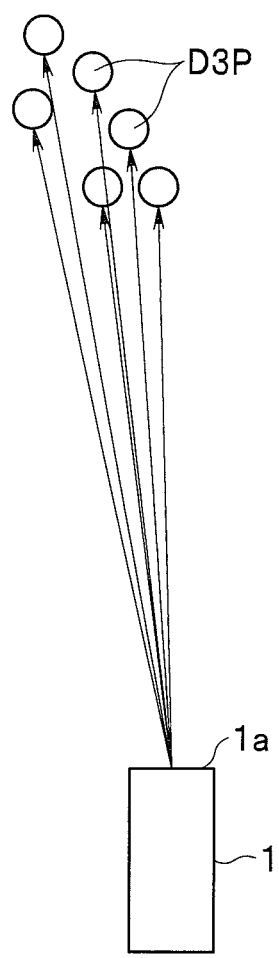
FIG. 6 is a diagram illustrating how a three-dimensional position estimated based on an image acquired when a distal end of an endoscope is at a certain position and the position of the distal end of the endoscope are connected to each other with a straight line in the above-described embodiment 1.

FIG. 6 is a diagram illustrating how the three-dimensional position D3P estimated based on an image acquired when the distal end 1a of the endoscope 1 is at a certain position and the position of the distal end 1a of the endoscope 1 are connected to each other with a straight line.

When the process in step S11 is finished, it is then judged whether or not unobserved three-dimensional positions D3P at which processing for taking one of the three-dimensional positions D3P as a position of interest has not been performed yet exist (step S12).

If it is judged that unobserved three-dimensional positions D3P exist, one unobserved three-dimensional position D3P for which the reliability is highest, for example, among the unobserved three-dimensional positions D3P is set to a three-dimensional position D3P of interest (step S13).

Note that setting the one unobserved three-dimensional positions D3P for which the reliability is highest is set to the three-dimensional position D3P of interest is to efficiently perform processing. Accordingly, if a high processing efficiency is not required, the three-dimensional positions D3P are not necessarily set to the three-dimensional position D3P of interest in descending order of reliability.

It is judged whether or not another three-dimensional position D3P other than the three-dimensional position D3P of interest exists on a straight line connecting the position of the distal end 1a of the endoscope 1 and the three-dimensional position D3P of interest (step S14). Note that in a combination of a mathematical point and a mathematical straight line, that is, a combination of a point having an infinitesimal size and a straight line having an infinitesimal thickness, it is very rare that a plurality of points exist on the straight line. In the judgment, at least one of the other three-dimensional position D3P and the straight line is treated as having a finite size (a three-dimensional solid that is neither a point nor a surface).

A first method of treating at least one of the other three-dimensional position D3P and the straight line as having a finite size is a method of calculating a conical surface contacting a region of a predetermined size (e.g., a sphere region having a predetermined radius) having the three-dimensional position D3P of interest as a center with the position of the distal end 1a of the endoscope 1 as a vertex and treating the straight line as a three-dimensional region (cone) within the conical surface to judge whether or not the cone crosses the other three-dimensional position D3P as a mathematical point.

A second method is a method of treating the straight line connecting the position of the distal end 1a of the endoscope 1 and the three-dimensional position D3P of interest as a column having a predetermined radius to judge whether or not the column crosses the other three-dimensional position D3P as a mathematical point.

Further, a third method is a method of treating the straight line connecting the position of the distal end 1a of the endoscope 1 and the three-dimensional position D3P of interest as a mathematical straight line but treating the other three-dimensional position D3P as a region having a predetermined size (e.g., a sphere region having a predetermined radius).

Note that the above-described first to third methods may be combined with one another. For example, although the straight line connecting the position of the distal end 1a of the endoscope 1 and the three-dimensional position D3P of interest is treated as a mathematical straight line in the third method. Alternatively, it may be judged whether or not the cone as described in the first method or the column as described in the second method crosses the other three-dimensional position D3P having a predetermined size.

In addition, although the size of the other three-dimensional position D3P or the straight line is made constant in the above-described first to third methods, the present invention is not limited to this. The size may be set depending on the reliability for the three-dimensional position D3P. For example, in the first or second method, the cone or the column may be calculated based on a radius corresponding to the reliability for the three-dimensional position D3P of interest. In the third method, the radius of the sphere region, for example, may be determined depending on the reliability for the other three-dimensional position D3P. As a specific relationship between a reliability and a radius (size), the radius may be made large when the reliability is high, and may be made small when the reliability is low (that is, the radius monotonously increases, as the reliability increases), for example.

If it is judged that another three-dimensional position D3P exists, it is judged whether or not the reliability for the three-dimensional position D3P of interest is not more than the reliability for the other three-dimensional position D3P (step S15).

If it is judged that the reliability for the three-dimensional position D3P of interest is more than the reliability for the other three-dimensional position D3P, the other three-dimensional position D3P is deleted (step S16).

Then, it is judged whether or not yet another three-dimensional position D3P exists on a straight line of interest (step S17).

If it is judged that yet another three-dimensional position D3P exists, the processing returns to step S15. In step S15, processing for comparing, based on the reliability for the three-dimensional position D3P of interest and the reliability for the yet other three-dimensional position D3P, the reliabilities and deleting the three-dimensional position D3P, as described above, is performed.

On the other hand, if it is judged that the reliability for the three-dimensional position D3P of interest is not more than the reliability for the other three-dimensional position D3P, the three-dimensional position D3P of interest is deleted (step S18).

Thus, the three-dimensional image generation unit 23 sets one of the plurality of three-dimensional positions D3P estimated by the three-dimensional position estimation unit 22 as the three-dimensional position D3P of interest, draws the straight line between the position of the distal end 1a of the endoscope 1 when the image based on which the three-dimensional position D3P of interest has been estimated has been acquired and the three-dimensional position D3P of interest, to compare the reliability for the other three-dimensional position D3P existing on the straight line with the reliability for the three-dimensional position D3P of interest, and deletes the three-dimensional position D3P of interest or the other three-dimensional position D3P for which the reliability is lower.

Note that the three-dimensional position D3P of interest is deleted to leave the other three-dimensional position D3P when the reliabilities are equal to each other in steps S15, S16, and S18. Conversely, processing may be performed to delete the other three-dimensional position D3P and leave the three-dimensional position D3P of interest. Alternatively, processing may be performed to newly calculate an average three-dimensional position D3P of the three-dimensional position D3P of interest and the other three-dimensional position D3P equal in reliability to the three-dimensional position D3P of interest to leave the calculated average three-dimensional position D3P and delete both the three-dimensional position D3P of interest and the other three-dimensional position D3P. Accordingly, deleting the three-dimensional position D3P of interest for which the reliability is lower is a basis of processing. However, when the plurality of three-dimensional positions D3P equal in reliability exist, it can be appropriately determined which of the three-dimensional positions D3P is to be deleted and which of the three-dimensional positions D3P is to be left.

If the process in step S18 is performed, if it is judged that yet another three-dimensional position D3P does not exist in step S17, or if it is judged that another three-dimensional position D3P does not exist on the straight line in step S14, the processing returns to step S12. In step S12, the above-described processing is performed.

Thus, if it is judged that the unobserved three-dimensional position D3P does not exist in step S12, the processing returns to the processing illustrated in FIG. 2.

Figure 7:
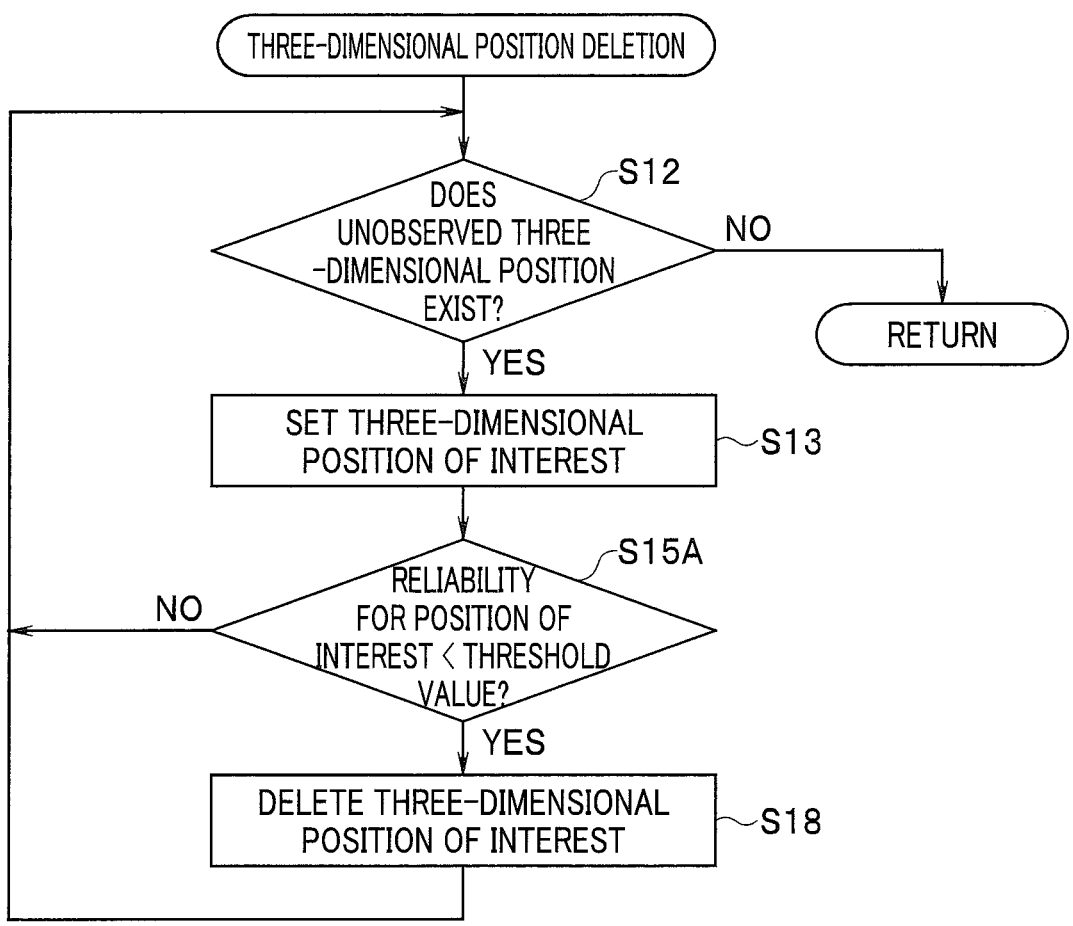
FIG. 7 is a flowchart illustrating a modification of three-dimensional position deletion processing in the endoscope system according to the above-described embodiment 1.

Then, FIG. 7 is a flowchart illustrating a modification of three-dimensional position deletion processing in the endoscope system.

When the processing is started, the processes in steps S12 and S13, described above, are performed. In step S13, any of the unobserved three-dimensional positions D3P may be set to the three-dimensional position D3P of interest, and the unobserved three-dimensional positions D3P need not be set in descending order of reliability.

It is judged whether or not the reliability for the three-dimensional position D3P of interest is less than a threshold value (step S15A). The threshold value used for the judgment may be a fixed value previously set, or may be a value calculated based on statistics of the respective reliabilities for all the three-dimensional positions D3P.

If it is judged that the reliability for the three-dimensional position D3P of interest is less than the threshold value, the process in step S18 is performed, to delete the three-dimensional position D3P of interest.

If the process in step S18 is performed, or it is judged that the reliability for the three-dimensional position D3P of interest is the threshold value or more in step S15A, the processing returns to step S12. In step S12, the above-described processing is performed.

Thus, if it is judged in step S12 that the unobserved three-dimensional position D3P does not exist, the processing returns to the processing illustrated in FIG. 2.

Note that although the three-dimensional image generation unit 23 calculates a polygon based on the three-dimensional positions D3P remaining as a result of deleting the three-dimensional position D3P for which the reliability is low, to generate a three-dimensional shape image, the remaining three-dimensional positions D3P also vary in reliability. The three-dimensional image generation unit 23 may generate a three-dimensional shape image that is made different in color between a polygon constructed from the three-dimensional position D3P for which the reliability is high and a polygon constructed from the three-dimensional position D3P for which the reliability is low (that is, is made different in color for each portion depending on the reliability) when generating the three-dimensional shape image. As a result, a user can simply identify a portion having a high shape reliability and a portion having a low shape reliability in the three-dimensional shape image only by seeing the three-dimensional shape image at a glance.

According to the embodiment 1, the reliability for the three-dimensional position D3P estimated by the three-dimensional position estimation unit 22 is judged based on the predetermined parameter related to the endoscope system. Therefore, the reliability for the estimated three-dimensional position D3P can be enhanced.

At this time, when the three-dimensional image generation unit 23 generates the three-dimensional shape image corresponding to the reliability, the three-dimensional shape image in which the reliability is enhanced can be observed.

Particularly, if the plurality of three-dimensional positions D3P for the target portion exist, the three-dimensional shape can be reproduced without being affected by the three-dimensional position D3P estimated to have a large error by deleting the three-dimensional position D3P other than the three-dimensional position D3P for which the reliability is highest and generating the three-dimensional shape image based on the three-dimensional positions D3P remaining after the deletion.

When one of the plurality of three-dimensional positions D3P is set to the three-dimensional position D3P of interest, the straight line is drawn between the position of the distal end 1a of the endoscope 1 when the image based on which the three-dimensional position D3P of interest has been estimated has been acquired and the three-dimensional position D3P of interest, to compare the reliability for the other three-dimensional position D3P existing on the straight line with the reliability for the three-dimensional position D3P of interest, and the three-dimensional position D3P of interest or the other three-dimensional position D3P for which the reliability is lower is deleted, the three-dimensional positions D3P that overlap each other when viewed from the endoscope 1 can be appropriately deleted.

Embodiment 2

Figure 8:
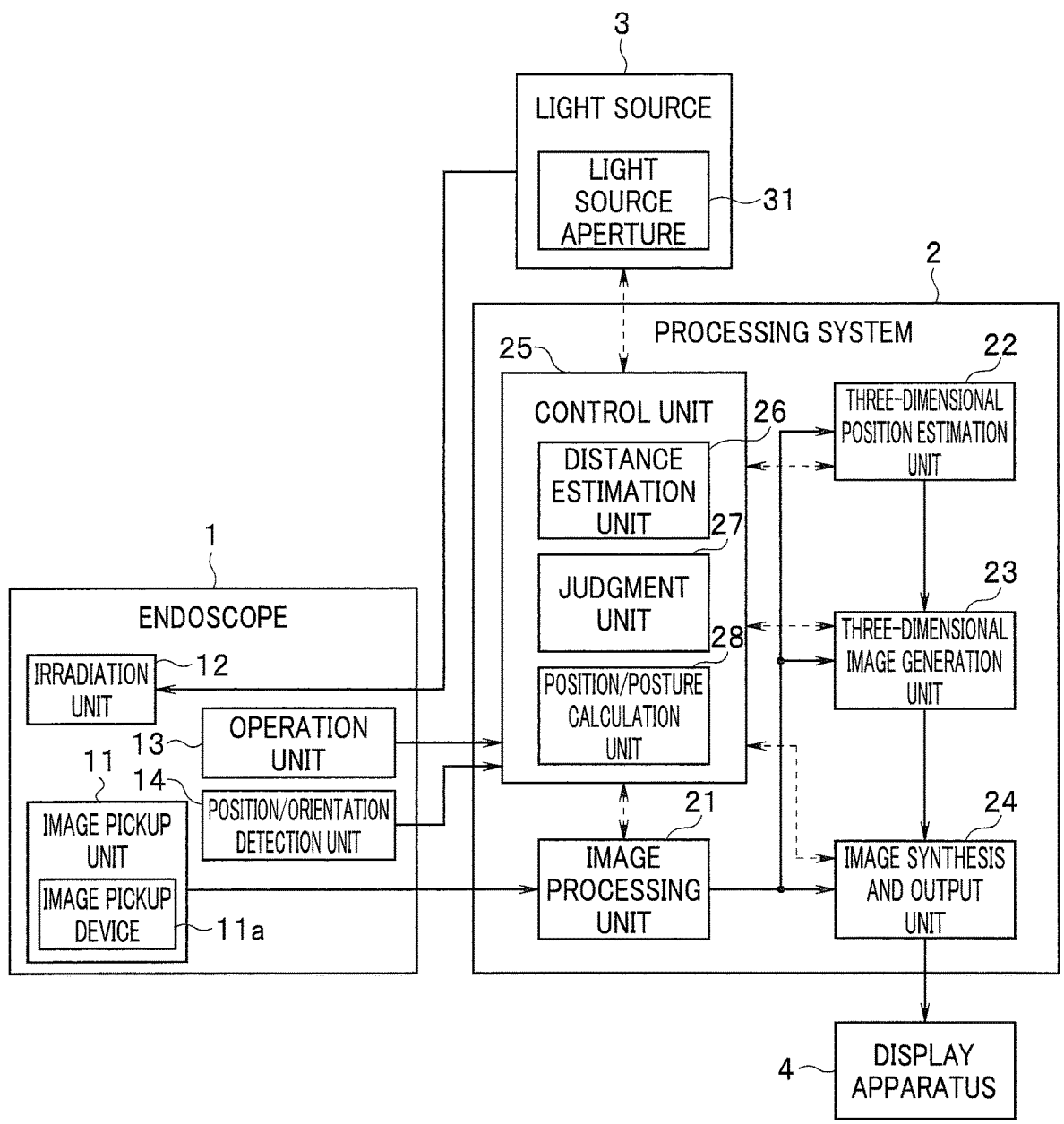
FIG. 8 is a block diagram illustrating a configuration of an endoscope system according to embodiment 2 of the present invention.

FIGS. 8 to 19 illustrate embodiment 2 of the present invention, where FIG. 8 is a block diagram illustrating a configuration of an endoscope system.

In the embodiment 2, similar units to the units in the above-described embodiment 1 are respectively assigned the same reference numerals, for example, to omit description, as needed, and different points will be mainly described.

Although it is assumed that the endoscope 1 is arranged in a fixed positional relationship with the subject in the above-described embodiment 1, it is assumed that an inside of a subject is observed while an endoscope 1 is inserted into the subject, that is, a positional relationship of the endoscope 1 with the subject changes in the present embodiment. Therefore, the endoscope system according to the present embodiment includes a position/posture information acquisition unit configured to acquire position information and posture information of the endoscope 1 in addition to the configuration illustrated in FIG. 1 in the embodiment 1.

First, in the configuration illustrated in FIG. 8, the endoscope 1 further includes a position/orientation detection unit 14 as a measurement section (sensor) arranged at a distal end 1a of an insertion section in the endoscope 1, for example, in addition to an image pickup unit 11, an irradiation unit 12, and an operation unit 13 described above.

The position/orientation detection unit 14 detects a position of the distal end 1a of the insertion section in the endoscope 1 to output a position detection signal while detecting a direction in which the distal end 1a of the insertion section in the endoscope 1 is directed to output an orientation detection signal. The position/orientation detection unit 14 detects coordinates on three axes (x-, y-, and z-axes) as spatial coordinates and respective angles around the three axes based on a magnetic field, for example, and is also referred to as a 6D sensor, for example.

A control unit 25 in a processing system 2 includes a position/posture calculation unit 28 in addition to a distance estimation unit 26 and a judgment unit 27.

The position/posture calculation unit 28 generates position information and posture information of the distal end 1a of the endoscope 1 based on the position detection signal and the orientation detection signal detected by the position/orientation detection unit 14.

Thus, the position/orientation detection unit 14 and the position/posture calculation unit 28 constitute the position/posture information acquisition unit configured to acquire the position information and the posture information of the endoscope 1.

The position information and the posture information of the endoscope 1 acquired by the position/posture calculation unit 28 are outputted to a three-dimensional position estimation unit 22. Thus, the three-dimensional position estimation unit 22 estimates the three-dimensional position D3P of the target portion within the subject further using the position information and the posture information acquired from the position/posture calculation unit 28 in addition to an image acquired from the endoscope 1.

Figure 9:
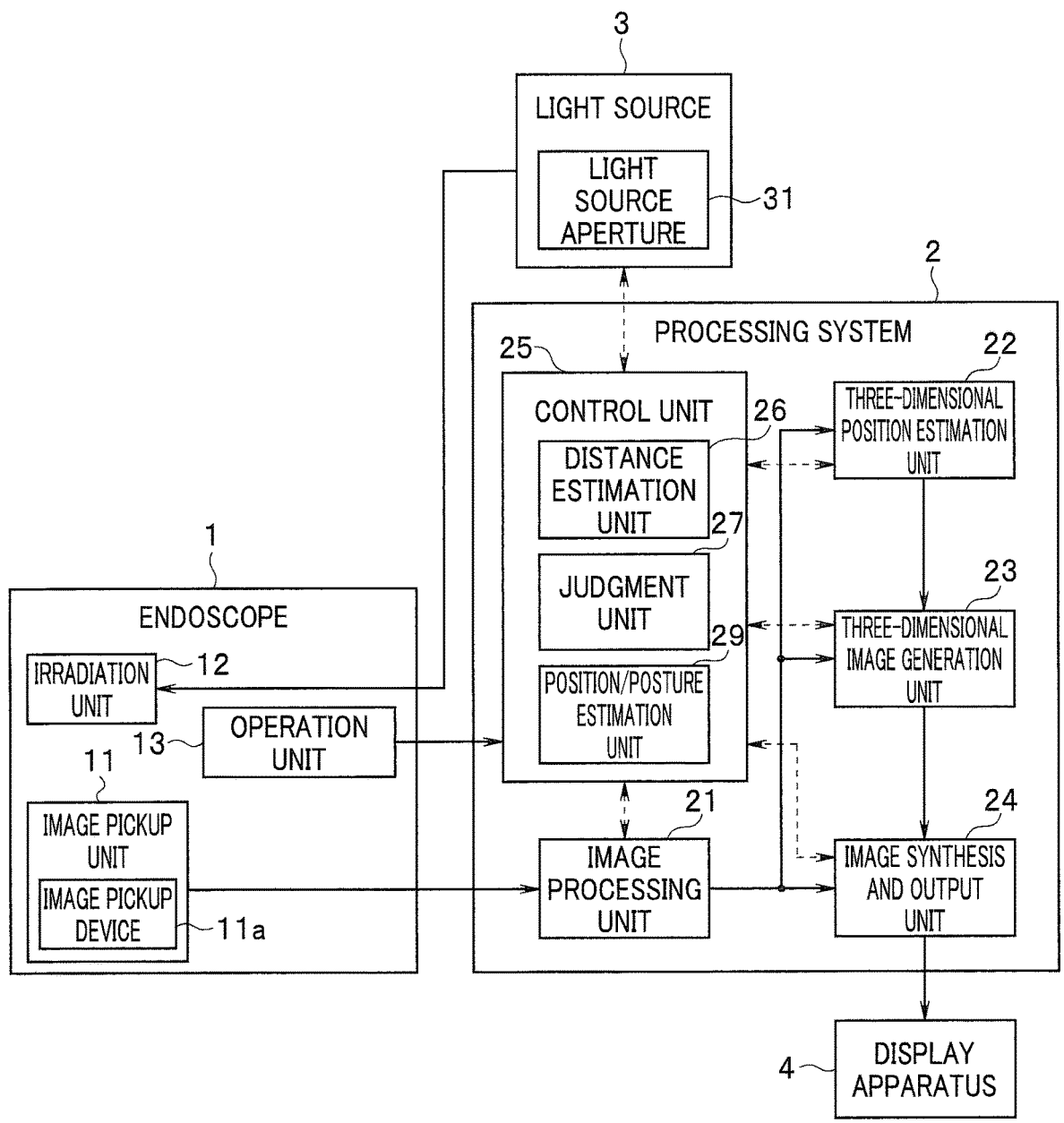
FIG. 9 is a block diagram illustrating a modification of the configuration of the endoscope system according to the above-described embodiment 2.

FIG. 9 is a block diagram illustrating a modification of the configuration of the endoscope system.

In the modification illustrated in FIG. 9, a position/posture estimation unit 29 is provided as a position/posture information acquisition unit within a control unit 25 in a processing system 2 instead of the position/orientation detection unit 14 and the position/posture calculation unit 28 illustrated in FIG. 8.

A technique for estimating position information and posture information of an endoscope 1 from an image or the like has been known in addition to a technique for detecting position information and posture information of the endoscope 1 using a sensor or the like. The position/posture estimation unit 29 estimates a position and a posture of the endoscope 1 by performing calculation or the like and acquires position information and posture information based on an image acquired by the endoscope 1, for example. The acquired position information and posture information of the endoscope 1 are used for estimating the three-dimensional position D3P by a three-dimensional position estimation unit 22, like in the foregoing.

Figure 10:
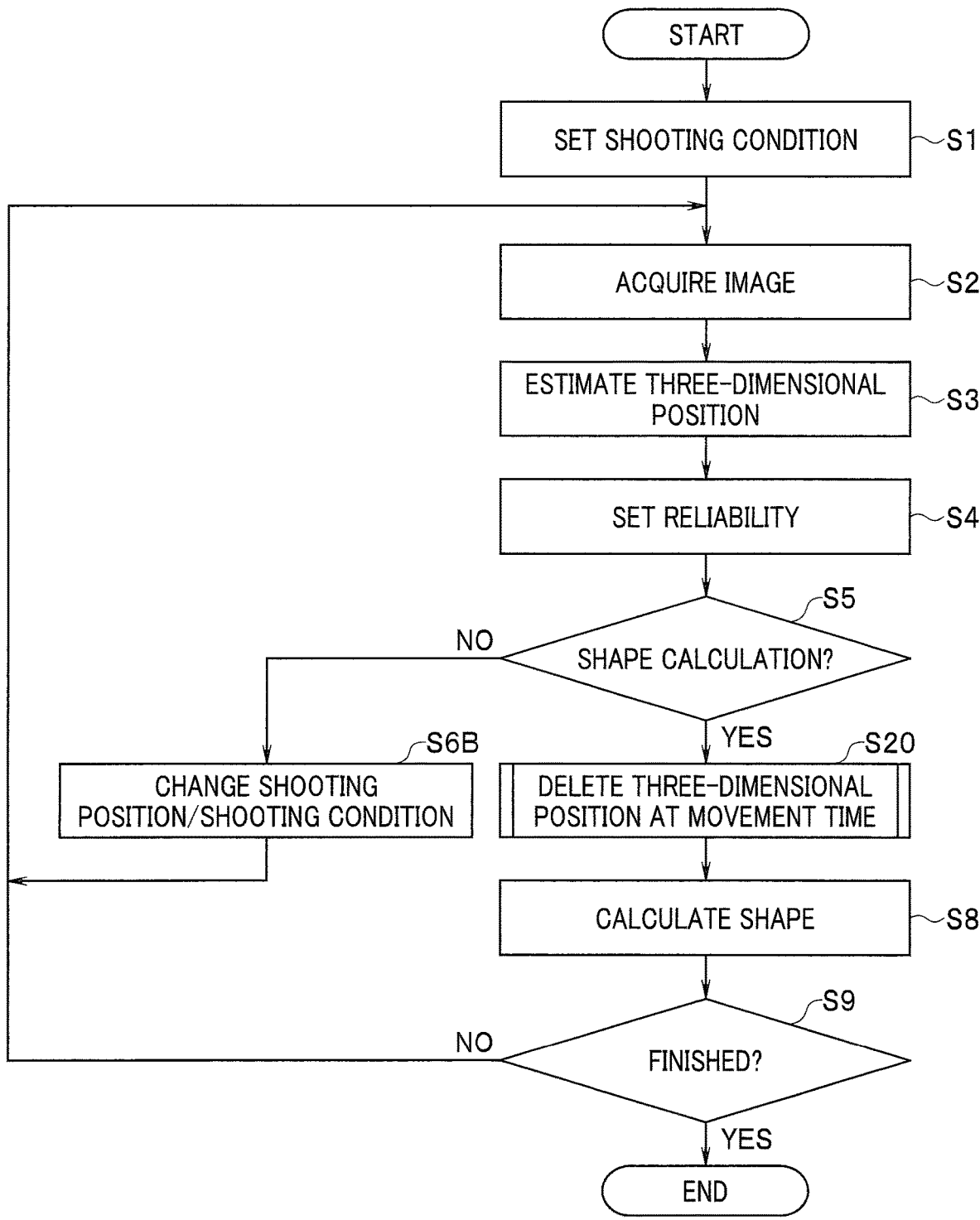
FIG. 10 is a flowchart illustrating a function of the endoscope system according to the above-described embodiment 2.

Then, FIG. 10 is a flowchart illustrating a function of the endoscope system.

When the processing is started, processes in steps S1 to S5 described above are performed.

If it is judged in step S5 that the processing does not proceed to shape calculation processing yet, a shooting position (including an orientation; the same applies hereinafter) changes as the endoscope 1 is inserted, for example, and the control unit 25 changes a shooting condition depending on a new shooting position (step S6B). Note that even if the shooting position does not change, like in the above-described embodiment 1, the shooting condition may be intentionally changed.

The above-described process in step S2 is performed under the changed shooting condition and shooting position, to acquire an image. When the processes in steps S2 to S6B are repeatedly performed a plurality of times, a plurality of images that differ in at least one of the shooting condition and the shooting position are acquired, and a plurality of three-dimensional positions D3P are estimated for the same target portion within the subject based on the acquired plurality of images.

Figure 12:
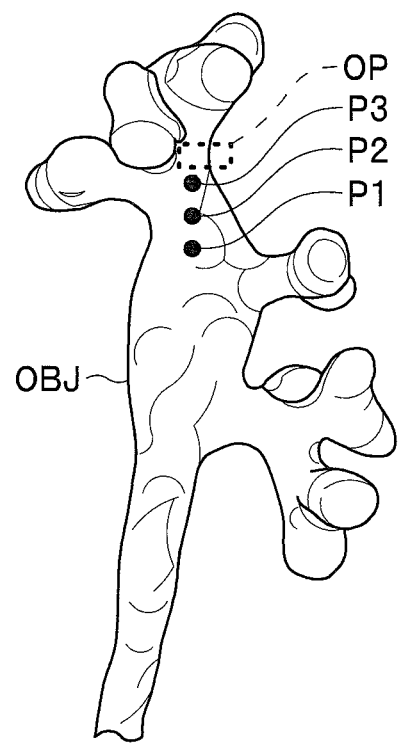
FIG. 12 is a diagram illustrating an example of a positional relationship between an image pickup position where an endoscope has acquired an image and a target portion within a subject in the above-described embodiment 2.

FIG. 12 is a diagram illustrating an example of a positional relationship between image pickup positions P1 to P3 where the endoscope 1 has acquired an image and a target portion OP within a subject OBJ.

When the endoscope 1 is inserted into the subject OBJ, the image pickup positions P1, P2, and P3 of the distal end 1a move in this order, for example. The image pickup positions P1 to P3 indicate that one image is acquired at the image pickup position P1, one image is acquired at the image pickup position P2 into which the endoscope 1 has been inserted, and one image is further acquired at the image pickup position P3 into which the endoscope 1 has been further inserted.

The way how the target portion OP appears in the acquired image also differs at the different image pickup positions.

Figure 13:
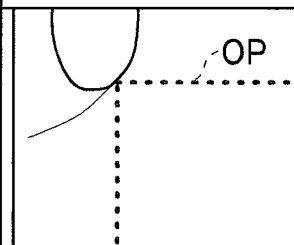
FIG. 13 is a chart illustrating a target portion in each of images respectively acquired at image pickup positions, a three-dimensional position estimated from the image, and a comprehensive total three-dimensional position in the above-described embodiment 2.
Figure 13:
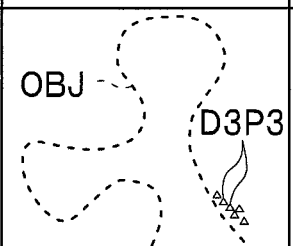
Figure 13:
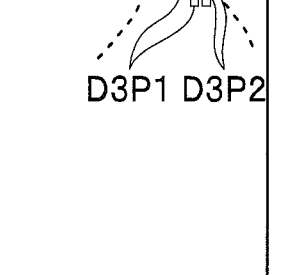
Figure 13:
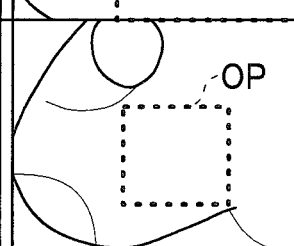
Figure 13:
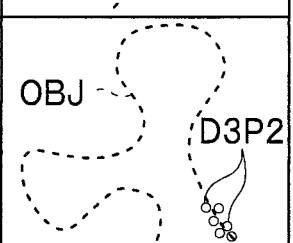
Figure 13:
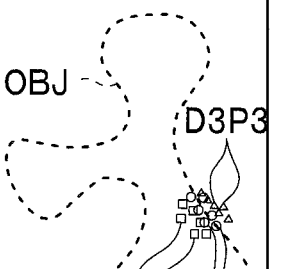
Figure 13:
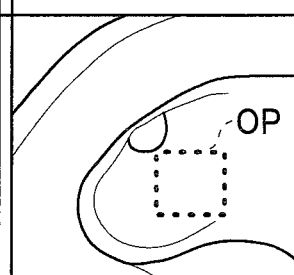

FIG. 13 is a chart illustrating the target portion OP in each of the images respectively acquired at the image pickup positions P1 to P3, the three-dimensional positions D3P respectively estimated from the images, and a comprehensive total three-dimensional position D3P.

In FIG. 13, the first vertical column from the left indicates which of P1 to P3, described above, is the image pickup position.

The second vertical column from the left indicates an image picked up at each of the image pickup positions and the target portion OP within the image. As the image pickup position comes close to the target portion OP, a size of the target portion OP within the image increases, as illustrated. Generally, if an orientation of the endoscope 1 changes, a position of the target portion OP within the image also changes.

The third column from the left indicates the three-dimensional position D3P estimated from the image picked up at each of the image pickup positions and an actual position of the subject OBJ in comparison. A three-dimensional position estimated from the image picked up at the image pickup position P1, a three-dimensional position estimated from the image picked up at the image pickup position P2, and a three-dimensional position estimated from the image picked up at the image pickup position P3 are respectively indicated by a square mark D3P1, a circular mark D3P2, and a triangular mark D3P3.

Further, the fourth column from the left collectively illustrates the three-dimensional positions D3P1 to D3P3 respectively estimated from the images picked up at the image pickup positions P1 to P3 in comparison with the actual position of the subject OBJ.

If it is judged in step S5 that the processing proceeds to shape calculation processing when the plurality of images are obtained, a three-dimensional image generation unit 23 performs three-dimensional position deletion processing at the time of movement, as described below with reference to FIG. 11 (step S20).

The three-dimensional image generation unit 23 generates a three-dimensional shape image, as described above, in step S8 based on the three-dimensional positions D3P remaining after the three-dimensional position D3P for which a reliability is low has been deleted.

Then, in step S9, it is judged whether or not the processing is finished. If it is judged that the processing is not finished, the processing returns to step S2. In step S2, subsequent image acquisition is performed. On the other hand, if it is judged that the processing is finished, the processing ends.

Figure 11:
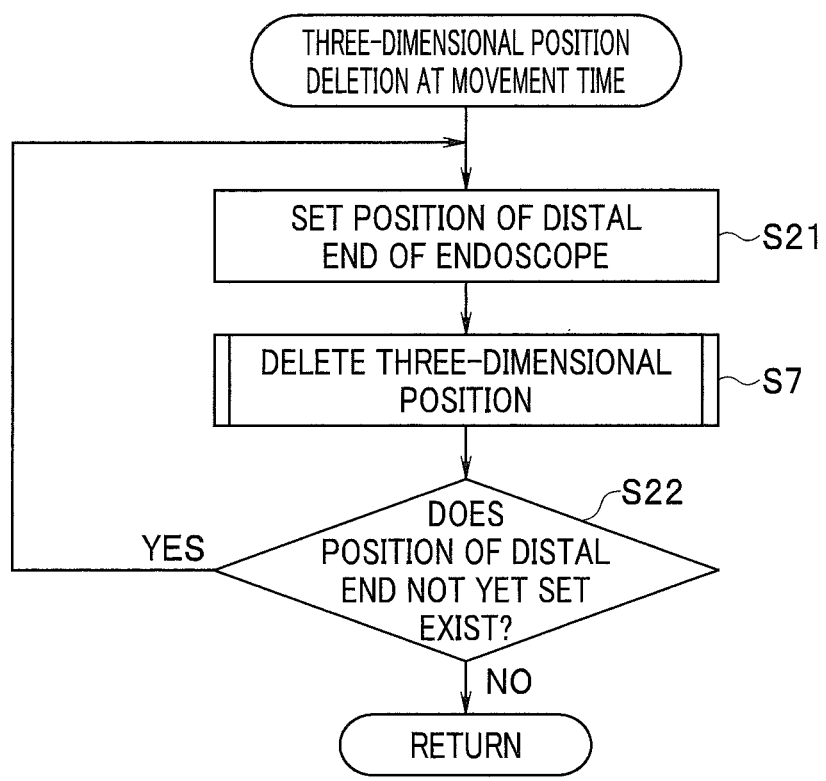
FIG. 11 is a flowchart illustrating three-dimensional position deletion processing at the time of movement in the endoscope system according to the above-described embodiment 2.

Then, FIG. 11 is a flowchart illustrating three-dimensional position deletion processing at the time of movement in the endoscope system.

If the processing is started in step S20 illustrated in FIG. 10, a position of the distal end 1a of the endoscope 1 in a space where the three-dimensional shape image is constructed is set based on position information of the endoscope 1 acquired by the position/posture information acquisition unit (the position/orientation detection unit 14 and the position/posture calculation unit 28 illustrated in FIG. 8 or the position/posture estimation unit 29 illustrated in FIG. 9) at the time of image acquisition (step S21).

If the position of the distal end 1a of the endoscope 1 is set, a position of the target portion relatively viewed from the position of the distal end 1a of the endoscope 1 is also determined in the space where the three-dimensional shape image is constructed.

In step S7, three-dimensional position deletion processing illustrated in FIG. 5 is performed by paying attention to the three-dimensional position D3P estimated based on an image acquired at the position of the distal end 1a of the endoscope 1 set in step S21.

Then, it is judged whether or not the position of the distal end 1a of the endoscope 1, which has not been set yet in step S21, exists (step S22).

If it is judged that the position of the distal end 1a of the endoscope 1, which has not been set yet, exists, the processing returns to step S21. In step S21, a subsequent position of the distal end 1a of the endoscope 1 is set, to perform processing as described above.

Figure 14:
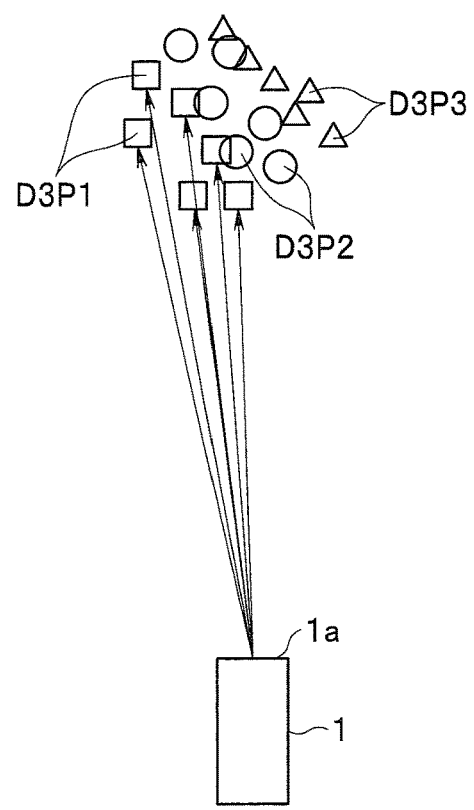
FIG. 14 is a diagram illustrating how a straight line is drawn from a position of a distal end of the endoscope to a three-dimensional position estimated from an image acquired at a first image pickup position in the above-described embodiment 2.
Figure 15:
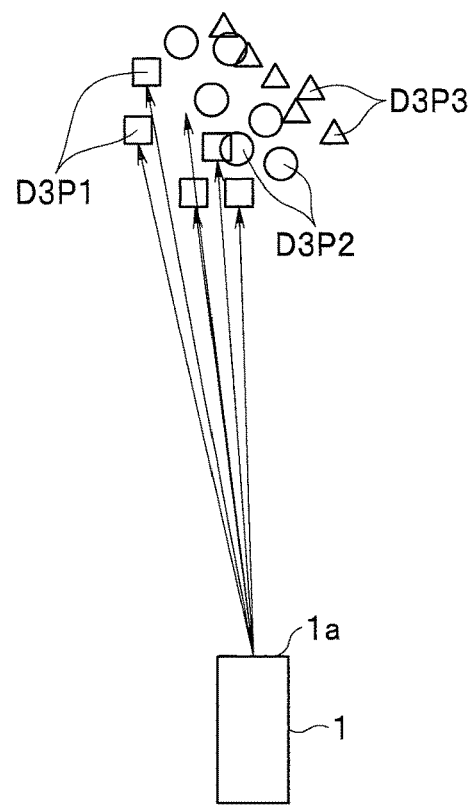
FIG. 15 is a diagram illustrating an example in which three-dimensional position deletion processing is performed based on the straight line drawn in FIG. 14 in the above-described embodiment 2.

FIG. 14 is a diagram illustrating how a straight line is drawn from the position of the distal end 1a of the endoscope 1 to the three-dimensional position D3P1 estimated from the image acquired at the first image pickup position P1, and FIG. 15 is a diagram illustrating an example in which three-dimensional position deletion processing is performed based on the straight line drawn in FIG. 14.

In step S21 illustrated in FIG. 11 described above, if the position of the distal end 1a of the endoscope 1 is set to the first image pickup position P1, the straight line as illustrated in FIG. 14 is drawn. If a plurality of three-dimensional positions D3P (as the three-dimensional positions D3P, respective three-dimensional positions related to images at other image pickup positions such as not only D3P1 but also D3P2 and D3P3 are included in a target) exist on one straight line, the three-dimensional position D3P for which the reliability is lower is deleted (when the respective reliabilities for the three-dimensional positions D3P are equal, any one of the three-dimensional positions D3P is left, or the above-described average three-dimensional position D3P is newly calculated and left and both the three-dimensional position D3P of interest and the other three-dimensional position D3P are deleted), as described in FIG. 5. The six three-dimensional positions D3P1 with square marks in FIG. 14 are changed to five three-dimensional positions D3P1 with square marks in FIG. 15 because one of the three-dimensional positions D3P1 is deleted after the three-dimensional position deletion processing is performed.

Figure 16:
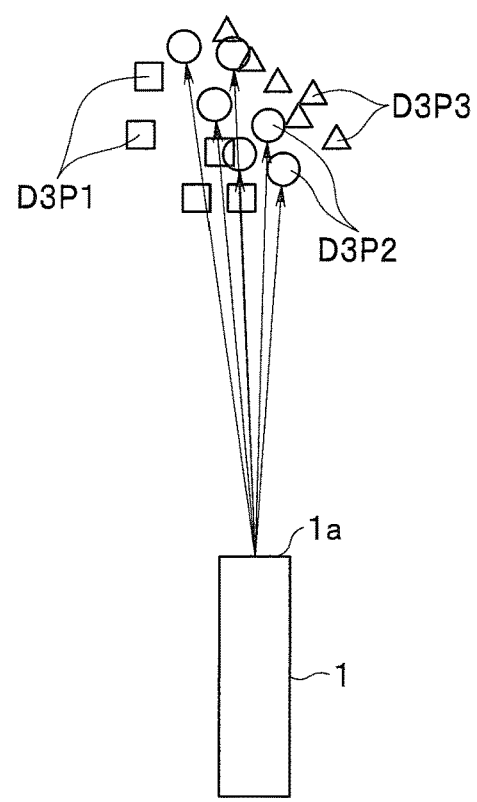
FIG. 16 is a diagram illustrating how a straight line is drawn from the position of the distal end of the endoscope to a three-dimensional position estimated from an image acquired at a second image pickup position in the above-described embodiment 2.
Figure 17:
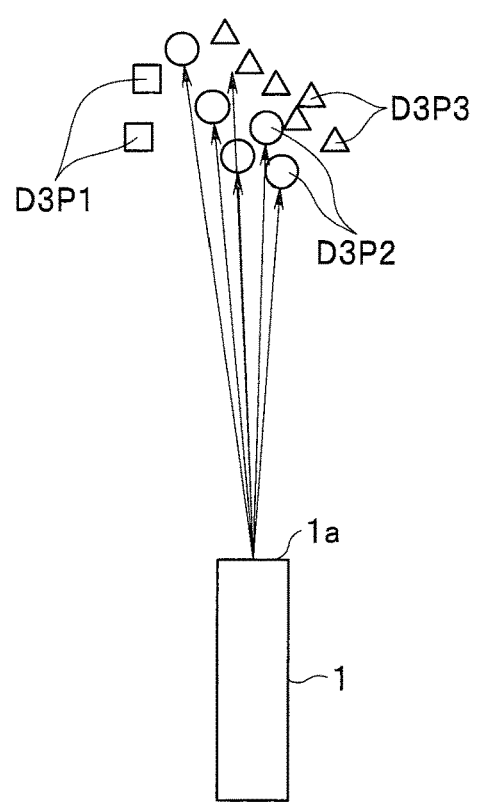
FIG. 17 is a diagram illustrating an example in which three-dimensional position deletion processing is performed based on the straight line drawn in FIG. 16 in the above-described embodiment 2.

Then, FIG. 16 is a diagram illustrating how a straight line is drawn from the position of the distal end 1a of the endoscope 1 to the three-dimensional position D3P2 estimated from the image acquired at the second image pickup position P2, and FIG. 17 is a diagram illustrating an example in which three-dimensional position deletion processing is performed based on the straight line drawn in FIG. 16.

If processing paying attention to the first image pickup position P1 ends, the processing returns to the process in step S21 from step S22 illustrated in FIG. 11. In step S21, similar processing is then performed by paying attention to the second image pickup position P2. In other words, if straight lines are respectively drawn from the position of the distal end 1a to the three-dimensional positions D3P2 and a plurality of three-dimensional positions D3P exist on the one straight line, as illustrated in FIG. 16, the three-dimensional position D3P for which the reliability is lower is deleted (when the respective reliabilities for the three-dimensional positions D3P are equal, any one of the three-dimensional positions D3P is left, or the above-described average three-dimensional position D3P is newly calculated and left, to delete both the three-dimensional position D3P of interest and the other three-dimensional position D3P).

More specifically, the five three-dimensional positions D3P1 with square marks and the six three-dimensional positions D3P2 with circular marks in FIG. 16 are respectively changed to two three-dimensional positions D3P1 with square marks and five three-dimensional positions D3P2 with circular marks because some of the three-dimensional positions are deleted in FIG. 17 after the three-dimensional position deletion processing is performed.

Figure 18:
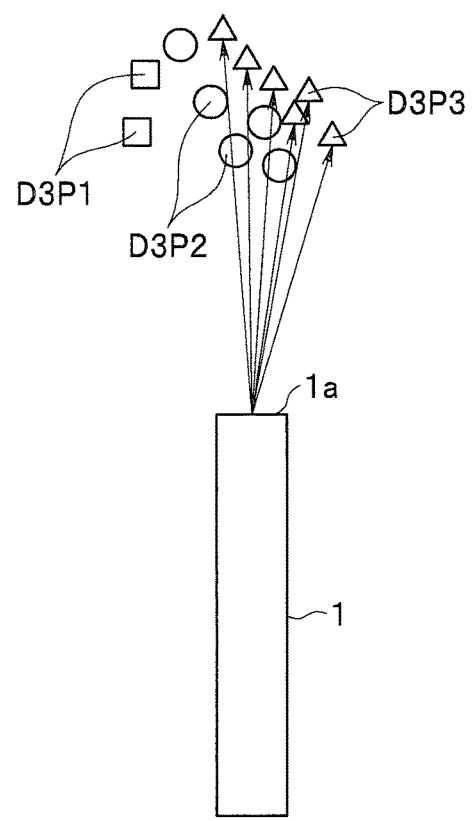
FIG. 18 is a diagram illustrating how a straight line is drawn from the position of the distal end of the endoscope to a three-dimensional position estimated from an image acquired at a third image pickup position in the above-described embodiment 2.
Figure 19:
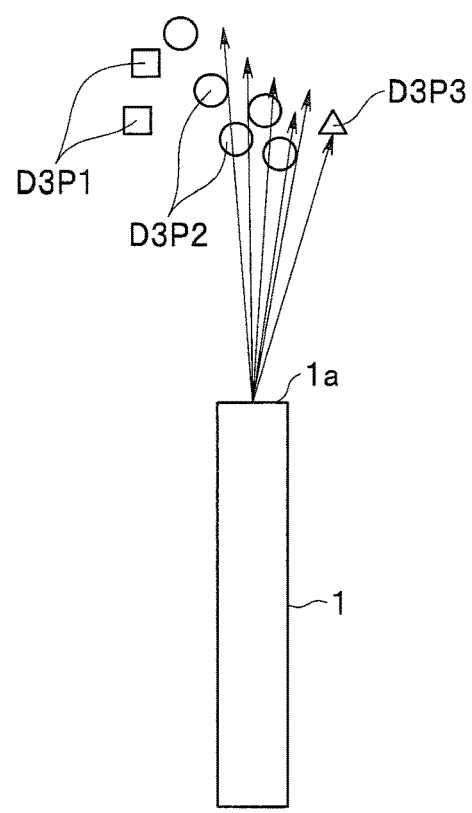
FIG. 19 is a diagram illustrating an example in which three-dimensional position deletion processing is performed based on the straight line drawn in FIG. 18 in the above-described embodiment 2.

FIG. 18 is a diagram illustrating how a straight line is drawn from the position of the distal end 1a of the endoscope 1 to the three-dimensional position D3P3 estimated from the image acquired at the third image pickup position P3, and FIG. 19 is a diagram illustrating an example in which three-dimensional position deletion processing is performed based on the straight line drawn in FIG. 18.

If processing paying attention to the second image pickup position P2 ends, the processing returns to the process in step S21 from step S22 illustrated in FIG. 11 again. In step S21, similar processing is then performed by paying attention to the third image pickup position P3. In other words, if straight lines are respectively drawn from the position of the distal end 1a to the three-dimensional positions D3P3 and a plurality of three-dimensional positions D3P exist on the one straight line, as illustrated in FIG. 18, the three-dimensional position D3P for which the reliability is lower is deleted (when the respective reliabilities for the three-dimensional positions D3P are equal, any one of the three-dimensional positions D3P is left, or the above-described average three-dimensional position D3P is newly calculated and left, to delete both the three-dimensional position D3P of interest and the other three-dimensional position D3P).

More specifically, the two three-dimensional positions D3P1 with square marks, the five three-dimensional positions D3P2 with circular marks, and the six three-dimensional positions D3P3 with triangular marks in FIG. 18 are respectively changed to two three-dimensional positions D3P1 with square marks, five three-dimensional positions D3P2 with circular marks, and one three-dimensional position D3P3 with a triangular mark because some of the three-dimensional positions are deleted in FIG. 19 after the three-dimensional position deletion processing is performed.

Thus, if the position of the distal end 1a of the endoscope 1, which has not been set yet, exists, subsequent positions of the distal end 1a are sequentially set in S21. As a result, if it is judged in step S22 that the position of the distal end 1a of the endoscope 1, which has not been set yet, does not exist, the processing returns to the processing illustrated in FIG. 10.

Note that although the image pickup positions where the images have been respectively picked up are moved in this order to perform processing, the present invention is not limited to this. Processing for drawing a straight line by paying attention to one three-dimensional position D3P regardless of the image pickup position and deleting, when a plurality of three-dimensional positions D3P exist on the straight line, the three-dimensional position D3P for which the reliability is lower (leaving, when the reliabilities for the three-dimensional positions D3P are equal, any one of the three-dimensional positions D3P or newly calculating and leaving the above-described average three-dimensional position D3P and deleting both the three-dimensional position D3P of interest and the other three-dimensional position D3P) may be performed while sequentially changing the three-dimensional position D3P to be paid attention to.

According to the embodiment 2, a substantially similar effect to that in the above-described embodiment 1 can be produced while the three-dimensional position D3P of the target portion OP is estimated using the position information and the posture information of the endoscope 1 acquired by the position/posture information acquisition unit. Accordingly, even when the same target portion OP is observed a plurality of times to estimate a shape while the endoscope 1 is moved, the shape can be correctly estimated, and thus can be correctly reproduced.

If the position/orientation detection unit 14 and the position/posture calculation unit 28 as a measurement section are used as the position/posture information acquisition unit, the position information and the posture information of the endoscope 1 can be accurately acquired based on a measurement result.

On the other hand, if the position/posture estimation unit 29 is used as the position/posture information acquisition unit, the position information and the posture information of the endoscope 1 can be acquired without using a configuration of a magnetic field generation apparatus, and the configuration can be simplified.

Embodiment 3

Figure 20:
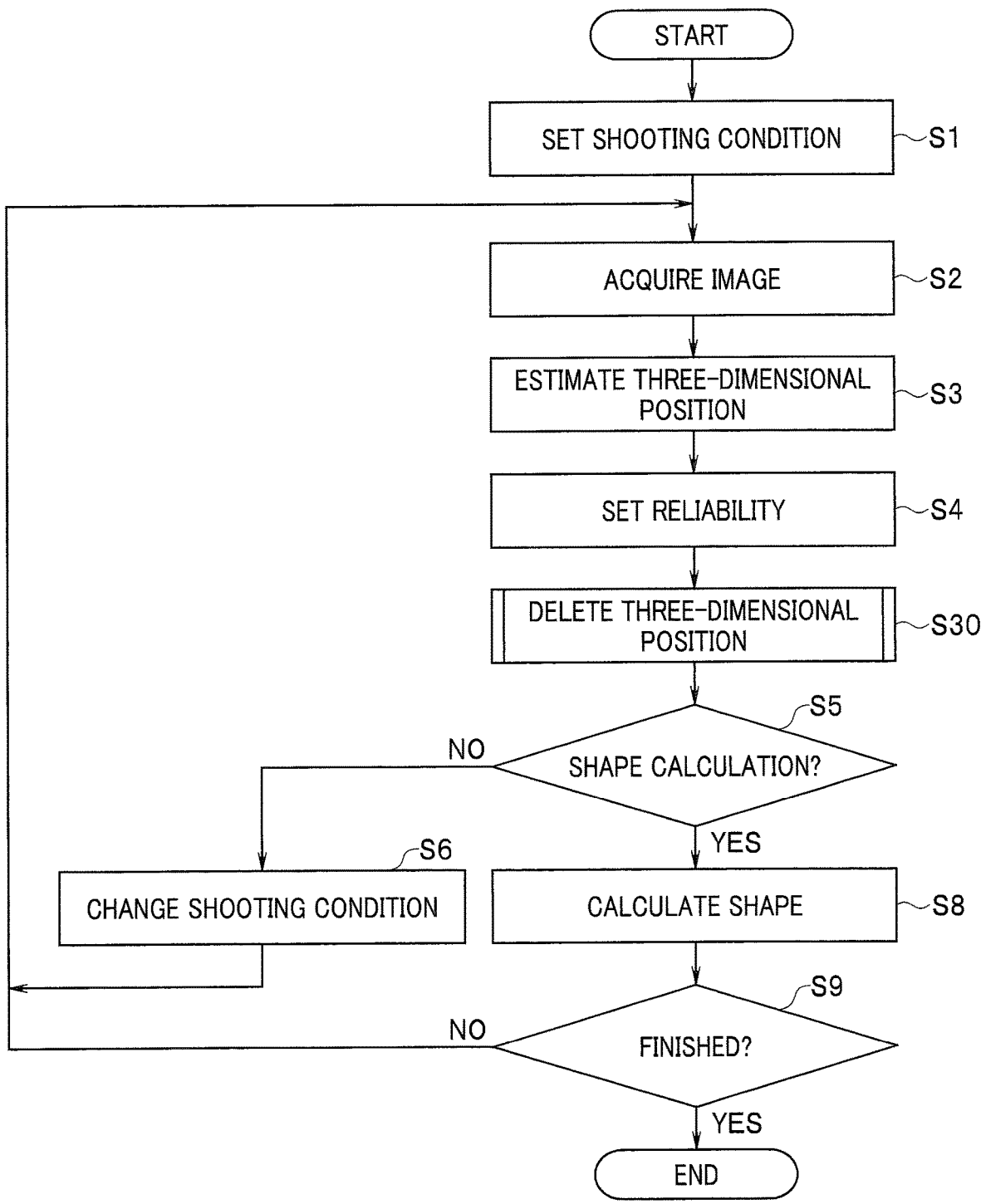
FIG. 20 is a flowchart illustrating a function of an endoscope system according to embodiment 3 of the present invention.

FIGS. 20 to 23 illustrate embodiment 3 of the present invention, where FIG. 20 is a flowchart illustrating a function of an endoscope system.

In the embodiment 3, similar units to the units in the above-described embodiments 1 and 2 are respectively assigned the same reference numerals, for example, to omit description, as needed, and different points will be mainly described.

The present embodiment is made different in a timing at which three-dimensional position deletion processing is performed and is made different in a method of performing the three-dimensional position deletion processing from the above-described embodiment 1. Note that although description is made using the embodiment 1 as a base, a change to at least either make the timing at which the three-dimensional position deletion processing is performed different or make the method of performing the three-dimensional position deletion processing different may be applied to both the embodiments 1 and 2 (that is, may be applied to both a case where a positional relationship of an endoscope 1 with a subject is fixed and a case where the positional relationship changes).

More specifically, when processing illustrated in FIG. 20 is started, the processes in steps S1 to S4 are performed, and three-dimensional position deletion processing is then performed (step S30).

More specifically, although it is judged that the processing proceeds to the shape calculation processing after finishing the plurality of images being acquired and the three-dimensional position deletion processing is then performed in the above-described embodiments 1 and 2, the three-dimensional position deletion processing is performed every time one image is acquired in the present embodiment.

Then, in step S5, it is judged whether or not the processing proceeds to shape calculation processing. If it is judged that the processing does not proceed to the shape calculation processing, the process in step S6 is performed. If it is judged that the processing proceeds to the shape calculation processing, the processes in steps S8 and S9 are started. If it is judged in step S9 that the processing is finished, the processing ends.

Figure 21:
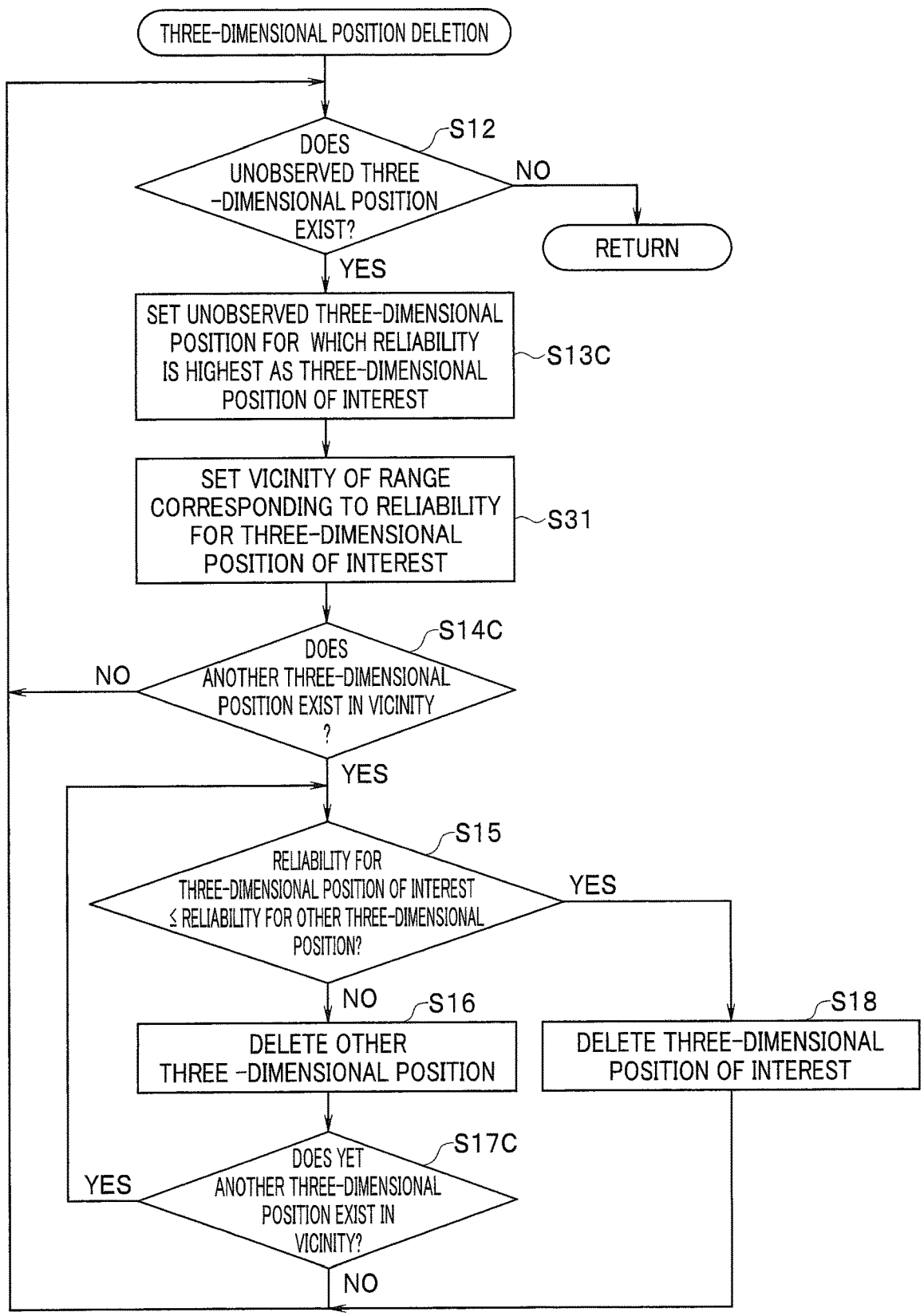
FIG. 21 is a flowchart illustrating three-dimensional position deletion processing in the endoscope system according to the above-described embodiment 3.

Then, FIG. 21 is a flowchart illustrating three-dimensional position deletion processing in the endoscope system.

When the processing is started, the process in step S12 is performed. If it is judged that unobserved three-dimensional positions D3P exist, the one unobserved three-dimensional position D3P for which a reliability is highest among the unobserved three-dimensional positions D3P is set to a three-dimensional position D3P of interest (step S13C).

Then, a vicinity of a range corresponding to the reliability for the three-dimensional position D3P of interest is set for the three-dimensional position D3P of interest (step S31).

Figure 22:
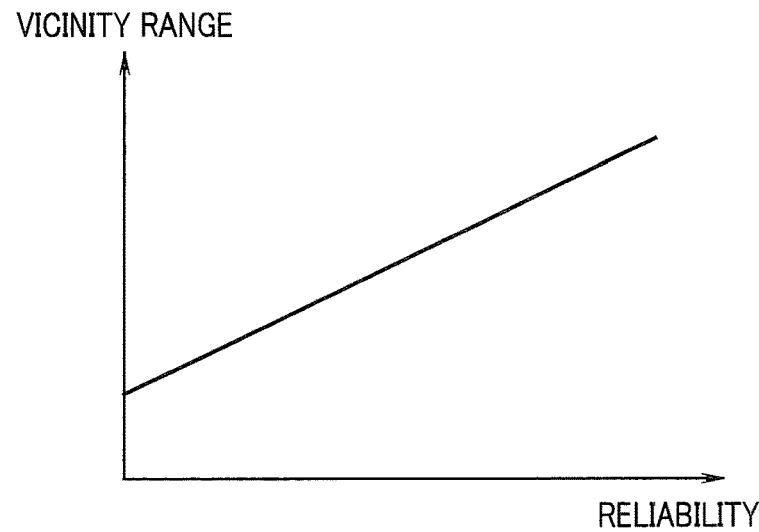
FIG. 22 is a line diagram illustrating an example of a size of a vicinity range set depending on a reliability set for a three-dimensional position of interest in the above-described embodiment 3.
Figure 23:
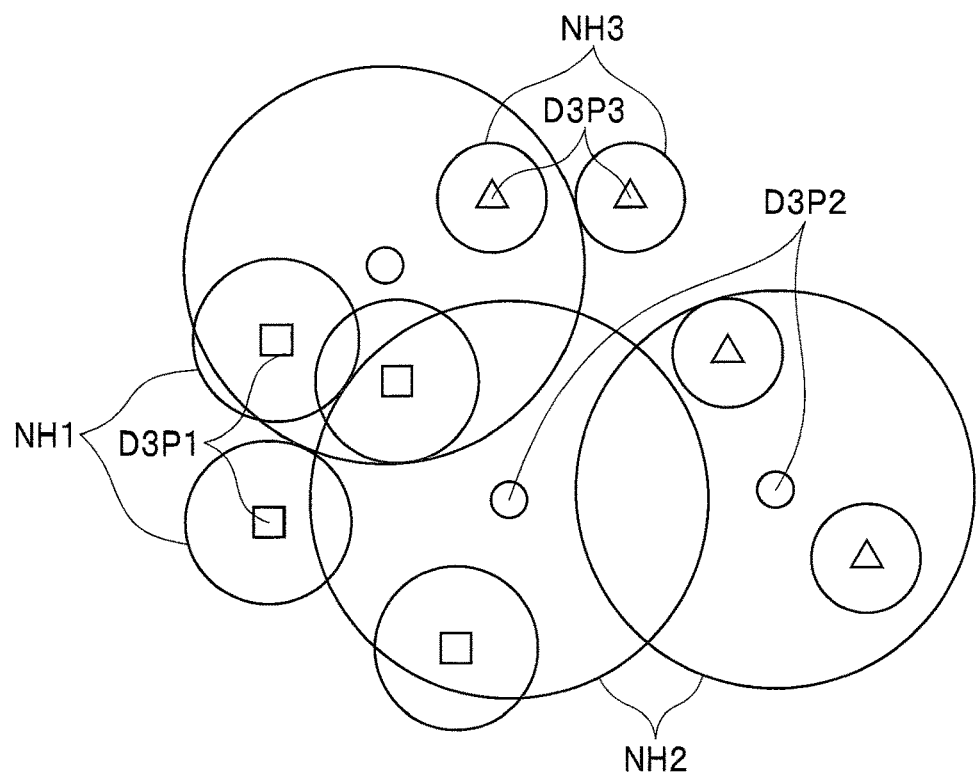
FIG. 23 is a line diagram illustrating an example of a vicinity range set depending on a reliability set for a three-dimensional position in the above-described embodiment 3.

FIG. 22 is a line diagram illustrating an example of a size of a vicinity range set depending on a reliability set for the three-dimensional position D3P of interest, and FIG. 23 is a line diagram illustrating an example of a vicinity range set depending on a reliability set for a three-dimensional position D3P.

First, setting is performed such that the higher the reliability is, the larger a vicinity range becomes, as illustrated in FIG. 22. As a result, a vicinity range NH2 of a three-dimensional position D3P2 for which a reliability is high is set largest, a vicinity range NH1 of a three-dimensional position D3P1 for which a reliability is medium is set smaller than the vicinity range NH2, and a vicinity range NH3 of a three-dimensional position D3P3 for which a reliability is small is set smaller than the vicinity range NH1.

Then, it is judged whether or not another three-dimensional position D3P exists in the vicinity range set for the three-dimensional position D3P of interest (step S14C).

If it is judged that another three-dimensional position D3P exists, the above-described process in step S15 and the process in step S16 or S18 is performed.

If the process in step S16 is performed, it is further judged whether or not yet another three-dimensional position D3P exists in the vicinity range set for the three-dimensional position D3P of interest (step S17C).

If it is judged that yet another three-dimensional position D3P exists, the processing returns to step S15. In step S15, processing for comparing, based on the reliability for the three-dimensional position D3P of interest and a reliability for the yet other three-dimensional position D3P, the reliabilities and deleting the three-dimensional position D3P, as described above, is performed.

Thus, the three-dimensional image generation unit 23 sets one of the plurality of three-dimensional positions D3P estimated by the three-dimensional position estimation unit 22 to the three-dimensional position D3P of interest, sets a vicinity range of a size corresponding to the reliability for the three-dimensional position D3P of interest, to compare the reliability for the other three-dimensional position D3P within the vicinity range with the reliability for the three-dimensional position D3P of interest, and deletes the three-dimensional position D3P of interest or the other three-dimensional position D3P for which the reliability is lower.

If the process in step S18 is performed, if it is judged in step S17C that yet another three-dimensional position D3P does not exist, or if it is judged in step S14C that another three-dimensional position D3P does not exist in the vicinity range, the processing returns to step S12. In step S12, the above-described processing is performed.

Thus, if it is judged in step S12 that the unobserved three-dimensional position D3P does not exist, the processing returns to the processing illustrated in FIG. 20.

According to the embodiment 3, a substantially similar effect to the effects in the above-described embodiments 1 and 2 can be produced while the vicinity range of the size corresponding to the reliability for the three-dimensional position D3P of interest is set, the reliability for the other three-dimensional position D3P within the vicinity range is compared with the reliability for the three-dimensional position D3P of interest, and the three-dimensional position D3P of interest or the other three-dimensional position D3P for which the reliability is lower is deleted. Accordingly, the plurality of three-dimensional positions D3P at positions in close proximity can be appropriately sort out depending on the respective reliabilities.

At this time, when the three-dimensional positions D3P of interest are set in descending order of reliability, efficient processing can be performed.

The three-dimensional position deletion processing is performed every time one image is acquired. Accordingly, a storage capacity of a memory storing the three-dimensional position D3P can be reduced. Further, the number of three-dimensional positions D3P to be managed is also reduced so that processing can be made higher in speed.

Embodiment 4

FIGS. 24 to 28 illustrate embodiment 4 of the present invention. In the embodiment 4, similar units to the units in the above-described embodiments 1 to 3 are respectively assigned the same reference numerals, to omit description, as needed, and different points will be mainly described.

In each of the above-described embodiments, the reliability has been set depending on the luminance of the target portion appearing in the image, as illustrated in FIG. 3 or 4.

On the other hand, the present embodiment provides various variations to setting of a reliability.

Figure 24:
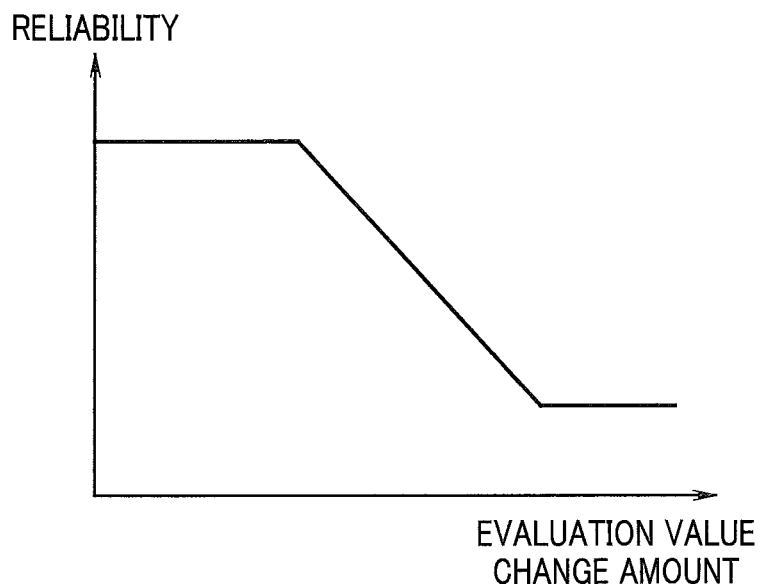
FIG. 24 is a line diagram illustrating an example in which a reliability for a three-dimensional position is set depending on an evaluation value change amount in embodiment 4 of the present invention.

First, FIG. 24 is a line diagram illustrating an example in which a reliability for a three-dimensional position D3P is set depending on an evaluation value change amount.

An evaluation value E is set depending on a light source aperture value F of a light source aperture 31, a gain G of an image pickup device 11a configured to acquire an image, and the like, and is described below using an evaluation function f as two variable functions F and G, for example.

$$E=f(F,G)$$

An evaluation value change amount $\Delta E$ indicating how the evaluation value E thus found has changed between frames is found by the following equation when an evaluation value in the current frame is represented by En and an evaluation value in a frame preceding the current frame by one frame is represented by E (n−1):

$$\Delta E=En-E(n-1)$$

When the evaluation value change amount $\Delta E$ is large, it is considered that a site to be an image pickup target has changed to a different site, for example, due to a change in direction of a distal end 1a of an endoscope 1, for example.

Therefore, a line diagram of FIG. 24 indicates how a reliability is set low when the evaluation value change amount $\Delta E$ is large.

Note that the above-described evaluation function is one example. Accordingly, an evaluation function using only either one of the light source aperture value F and the gain G may be used, or an evaluation function such as a multi-variable function a value of which changes depending on another variable may be used.

Figure 25:
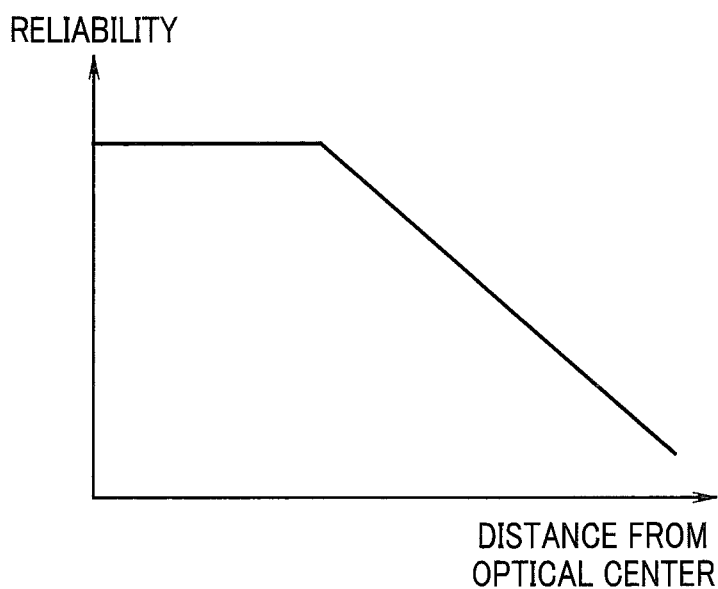
FIG. 25 is a line diagram illustrating an example in which a reliability for a three-dimensional position is set depending on a distance of a pixel in which a target portion the three-dimensional position of which has been acquired appears from an optical center in an image in the above-described embodiment 4.

Then, FIG. 25 is a line diagram illustrating an example in which a reliability for a three-dimensional position D3P is set depending on a distance of a pixel in which a target portion the three-dimensional position D3P of which has been acquired appears from an optical center in an image.

An objective optical system in the endoscope 1 is generally at a wide angle. Accordingly, a distortion exists at a periphery of the image. When the three-dimensional position D3P is estimated, the image the distortion of which has been corrected is used. However, a spacing between pixels to be used is widened toward the periphery of the image so that an error in correction increases. Accordingly, an image quality is lower in a peripheral portion of the image than in a central portion of the image. In an example illustrated in FIG. 25, a reliability in the peripheral portion where the image quality is low is made lower than a reliability in a region where an image quality is kept relatively high.

Note that although an example in which the reliability for the three-dimensional position D3P is set depending on the distance from the optical center has been described, a difference in image quality does not necessarily depend only on the distance (e.g. an image quality differs in a right-to-left direction and an up-and-down direction even if the distance from the optical center is the same). Therefore, more generally, the reliability for the three-dimensional position D3P may be set depending on a position of the target portion appearing in the image relative to the optical center in the image. For example, the image may be divided into a plurality of regions depending on the position relative to the optical center, to provide a reliability for each of the regions. Alternatively, a table describing a correspondence between the position relative to the optical center and the reliability may be created and stored in a storage section within the control unit 25.

Figure 26:
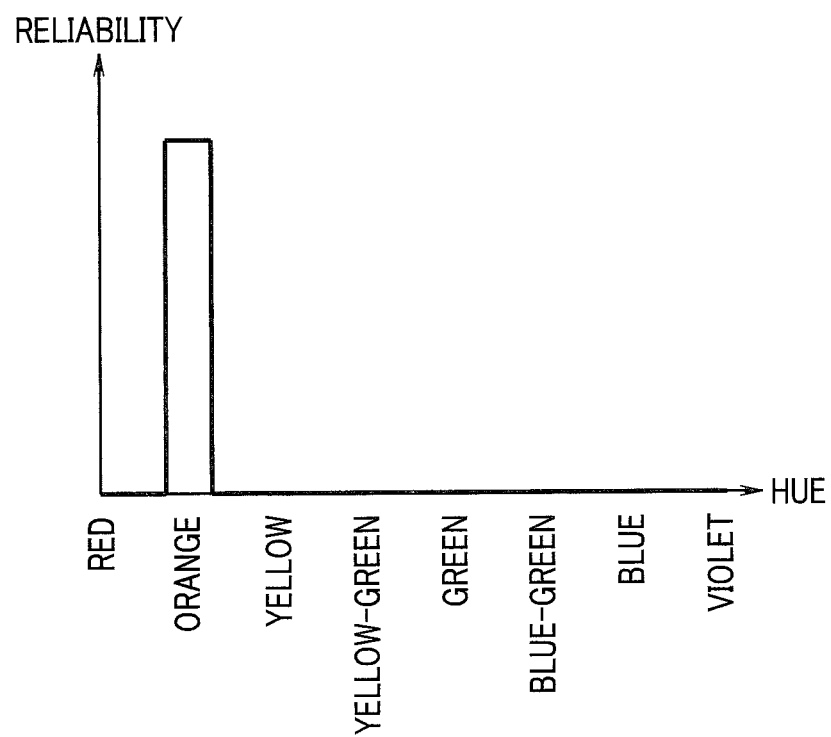
FIG. 26 is a line diagram illustrating an example in which a reliability for a three-dimensional position is set depending on a hue of a pixel in which a target portion the three-dimensional position of which has been acquired appears in the above-described embodiment 4.

Then, FIG. 26 is a line diagram illustrating an example in which a reliability for a three-dimensional position D3P is set depending on a hue of a pixel in which a target portion the three-dimensional position D3P of which has been acquired appears.

If the endoscope 1 is a medical endoscope, for example, a large part of an inside of a body cavity as a subject falls in a specific hue region. In the example illustrated in FIG. 26, a predetermined reliability is provided only when a hue in a target portion appearing in an image enters a hue region in the vicinity of orange between red and yellow, and the reliability is made low (the reliability is set to zero in this example) when the hue is another hue.

Even if a distance from the distal end 1a of the endoscope 1 is the same, for example, a luminance differs between a blood vessel portion within the body cavity and a portion other than the blood vessel portion. Therefore, when a distance to the target portion is estimated based on the luminance, the distance to the target portion may be measured as different distances, respectively, in the blood vessel portion and the portion other than the blood vessel portion.

On the other hand, the blood vessel portion and the portion other than the blood vessel portion differ not only in luminance but also in hue. When setting to provide a predetermined reliability only to a specific hue region as illustrated in FIG. 26 is performed, an accuracy of the three-dimensional position D3P to be estimated can be improved without being easily affected by a blood vessel or the like.

Figure 27:
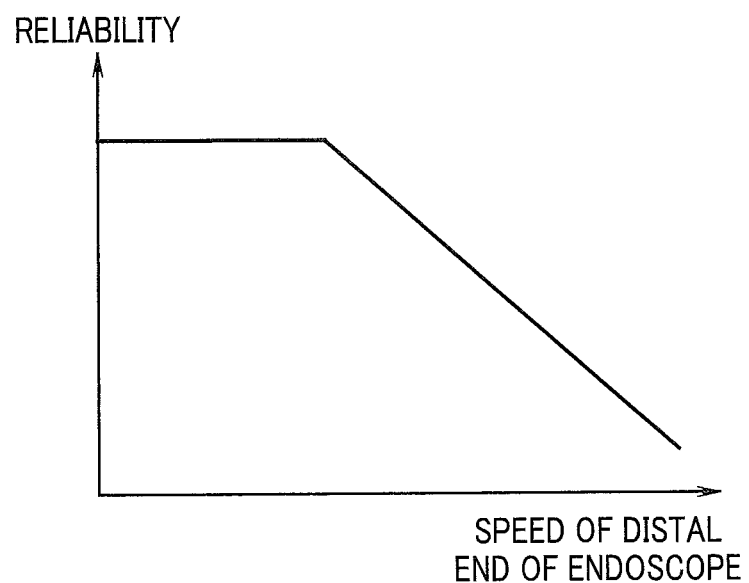
FIG. 27 is a line diagram illustrating an example in which a reliability for a three-dimensional position is set depending on a movement speed of a distal end of an endoscope in the above-described embodiment 4.

FIG. 27 is a line diagram illustrating an example in which a reliability for a three-dimensional position D3P is set depending on a movement speed of the distal end 1a of the endoscope 1.

When the movement speed of the distal end 1a of the endoscope 1 is large, a blur occurs in an image to be acquired. Therefore, when the movement speed of the distal end 1a of the endoscope 1 is a predetermined value or more, the reliability is set low depending on a magnitude of the movement speed. Note that the movement speed of the distal end 1a of the endoscope 1 can be calculated based on position information of a plurality of frames acquired by a position/orientation detection unit 14 and a position/posture calculation unit 28 illustrated in FIG. 8, for example. A speed sensor or the like may be separately provided at the distal end 1a of the endoscope 1 to detect the movement speed.

Figure 28:
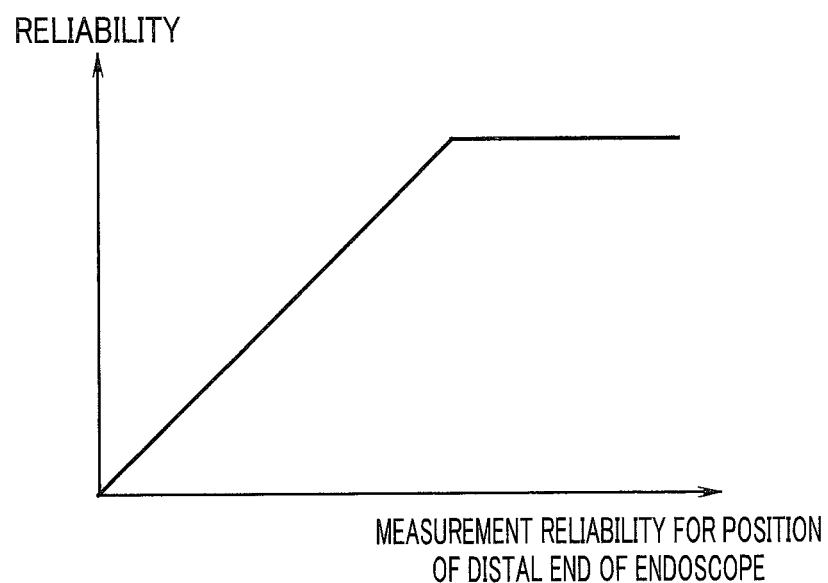
FIG. 28 is a line diagram illustrating an example in which a reliability for a three-dimensional position is set depending on a measurement reliability for a position of the distal end of the endoscope in the above-described embodiment 4.

FIG. 28 is a line diagram illustrating an example in which a reliability for a three-dimensional position D3P is set depending on a measurement reliability for a position of the distal end 1a of the endoscope 1.

The position/orientation detection unit 14 and the position/posture calculation unit 28 as a measurement section, as illustrated in FIG. 8, are used as a position/posture information acquisition unit (more specifically, when a magnetic field sensor or the like is used), a measurement reliability indicating how high a reliability for a measurement value is obtained.

The reliability for the three-dimensional position D3P to be estimated based on the position of the distal end 1a of the endoscope 1 for which the measurement reliability is high is high. Conversely, the reliability for the three-dimensional position D3P to be estimated based on the position of the distal end 1a of the endoscope 1 for which the measurement reliability is low is low.

Therefore, when the measurement reliability for the position of the distal end 1a of the endoscope 1 is lower than a predetermined value, the reliability for the three-dimensional position D3P is set low depending on the low measurement reliability.

Although only one of the above-described several reliability setting methods may be used, the plurality of reliability setting methods may be combined with one another.

For example, when a reliability set based on a luminance of a target portion appearing in an image is C1 (FIG. 3 or FIG. 4), a reliability set based on an evaluation value change amount $\Delta E$ is C2 (FIG. 24), a reliability set based on a distance from an optical center (more generally, a position relative to the optical center) is C3 (FIG. 25), a reliability set based on a hue is C4 (FIG. 26), a reliability set based on a movement speed of the distal end 1a of the endoscope 1 is C5 (FIG. 27), and a reliability set based on a measurement reliability for a position of the distal end 1a of the endoscope 1 is C6 (FIG. 28), a total reliability C may be found by an evaluation function C using the six reliabilities C1, C2, C3, C4, C5, and C6.

$$C=C(C1,C2,C3,C4,C5,C6)$$

According to the embodiment 4, a substantially similar effect to the effects in the above-described embodiments 1 to 3 is produced while the reliability for the three-dimensional position D3P is judged using as a predetermined parameter at least one of a luminance of a target portion appearing in an image, a light source aperture value for controlling a light amount of illumination light to be radiated onto a subject, a gain of an image pickup device configured to acquire an image, a position of the target portion appearing in the image relative to an optical center of the image, a hue of the target portion appearing in the image, a movement speed of the distal end 1a of the endoscope 1, and a reliability for a measurement value by a measurement section. Accordingly, an accuracy of the reliability can be improved. As a result, shape reproducibility of a three-dimensional shape image to be generated by a three-dimensional image generation unit 23 can be improved.

Further, if the above-described total reliability C is used, the reliability for the three-dimensional position D3P can be set with higher accuracy, and the shape reproducibility of the three-dimensional shape image can be further improved.

While the endoscope system has been mainly described above, the present invention includes an endoscope image processing method, and a non-transitory computer readable recording medium storing an endoscope processing program to be executed by a computer.

Further, the present invention is not limited to the above-described embodiments as they are, but can be embodied by modifying components without departing from the scope of the invention in a stage of implementation. Various aspects of the invention can be formed by an appropriate combination of a plurality of components disclosed in the above-described embodiments. For example, some of all the components illustrated in the embodiments may be deleted. Further, the components over the different embodiments may be combined, as needed. Accordingly, it goes without saying that various modifications and applications are possible without departing from the spirit of the invention.

What is claimed is:

1. An endoscope system comprising:
an endoscope configured to pick up an image of an inside of a subject to acquire an image; and
a processor including hardware,
wherein the processor is configured to
estimate a three-dimensional position of a target portion within the subject based on a predetermined image acquired by the endoscope,
set, for the estimated three-dimensional position, a reliability corresponding to a predetermined parameter related to the endoscope system determined when the predetermined image is acquired, and
select, when a plurality of three-dimensional positions for the target portion exist, a predetermined three-dimensional position among the plurality of three-dimensional positions depending on the set reliability and generate a three-dimensional shape image based on the selected predetermined three-dimensional position.

2. The endoscope system according to claim 1, wherein the processor selects the three-dimensional position for which the reliability is highest as the predetermined three-dimensional position.

3. The endoscope system according to claim 2, wherein the processor sets one of the estimated plurality of three-dimensional positions as a three-dimensional position of interest, draws a straight line between a position of a distal end of the endoscope when the image based on which the three-dimensional position of interest is estimated is acquired and the three-dimensional position of interest, to compare a reliability for another three-dimensional position on the straight line with a reliability for the three-dimensional position of interest, and selects the three-dimensional position of interest or the other three-dimensional position for which the reliability is higher.

4. The endoscope system according to claim 3, wherein the processor sets the estimated plurality of three-dimensional positions to the three-dimensional position of interest in descending order from the three-dimensional position for which the reliability is highest.

5. The endoscope system according to claim 2, wherein the processor sets one of the estimated plurality of three-dimensional positions to a three-dimensional position of interest, sets a vicinity range of a size corresponding to a reliability for the three-dimensional position of interest, to compare a reliability for another three-dimensional position within the vicinity range with the reliability for the three-dimensional position of interest, and selects the three-dimensional position of interest or the other three-dimensional position for which the reliability is higher.

6. The endoscope system according to claim 5, wherein the processor sets the estimated plurality of three-dimensional positions to the three-dimensional position of interest in descending order from the three-dimensional position for which the reliability is highest.

7. The endoscope system according to claim 1, wherein the processor selects, among the estimated plurality of three-dimensional positions, the three-dimensional position for which the reliability is judged to be higher than a threshold value as the predetermined three-dimensional position.

8. The endoscope system according to claim 1, wherein the processor generates the three-dimensional shape image that is made different in color for each portion depending on the reliability.

9. The endoscope system according to claim 1, wherein the processor
estimates a distance between the endoscope and the subject based on the image, and
estimates the three-dimensional position of the target portion based on the estimated distance and a position of the target portion in the image.

10. The endoscope system according to claim 1, wherein the processor
acquires position information and posture information of the endoscope, and
estimates the three-dimensional position of the target portion further using the position information and the posture information.

11. The endoscope system according to claim 10, comprising
a sensor configured to measure a position and a posture of the endoscope, to acquire the position information and the posture information.

12. The endoscope system according to claim 11, wherein the predetermined parameter includes at least one of a luminance of the target portion appearing in the image, a light source aperture value for controlling a light amount of illumination light radiated onto the subject, a gain of an image pickup device configured to acquire the image, a position of the target portion appearing in the image relative to an optical center of the image, a hue of the target portion appearing in the image, a movement speed of a distal end of the endoscope, and a reliability for a measurement value by the sensor.

13. The endoscope system according to claim 10, wherein the processor estimates a position and a posture of the endoscope based on the image acquired by the endoscope, to acquire the position information and the posture information.

14. An endoscope image processing method comprising:
estimating a three-dimensional position of a target portion within a subject based on a predetermined image acquired by image pickup of an inside of the subject by an endoscope;
setting for the estimated three-dimensional position a reliability corresponding to a predetermined parameter related to an endoscope system determined when the predetermined image is acquired; and
selecting, when a plurality of three-dimensional positions for the target portion exist, a predetermined three-dimensional position among the plurality of three-dimensional positions depending on the set reliability and generating a three-dimensional shape image based on the selected predetermined three-dimensional position.

15. A non-transitory computer readable recording medium storing an endoscope image processing program to be executed by a computer, the computer readable recording medium
estimating, when a processor executes the endoscope image processing program, a three-dimensional position of a target portion within a subject based on a predetermined image acquired by image pickup of an inside of the subject by an endoscope;
setting for the estimated three-dimensional position a reliability corresponding to a predetermined parameter related to the endo scope system determined when the predetermined image is acquired, and
selecting, when a plurality of three-dimensional positions for the target portion exist, a predetermined three-dimensional position among the plurality of three-dimensional positions depending on the set reliability and generating a three-dimensional shape image based on the selected predetermined three-dimensional position.

* * * * *